US008053410B2

(12) United States Patent
Klausen et al.

(10) Patent No.: US 8,053,410 B2
(45) Date of Patent: Nov. 8, 2011

(54) PEGYLATED FACTOR VII GLYCOFORMS

(75) Inventors: Niels Kristian Klausen, Gentofte (DK); Soren Bjorn, Lyngby (DK); Carsten Behrens, Kobenhavn N (DK); Patrick William Garibay, Holte (DK)

(73) Assignee: Novo Nordisk Health Care A/G, Zurich (CH)

( * ) Notice: Subject to any disclaimer, the term of this patent is extended or adjusted under 35 U.S.C. 154(b) by 0 days.

(21) Appl. No.: 12/371,156

(22) Filed: Feb. 13, 2009

(65) Prior Publication Data

US 2009/0227504 A1    Sep. 10, 2009

Related U.S. Application Data

(63) Continuation of application No. 11/845,175, filed on Aug. 27, 2007, now abandoned, which is a continuation of application No. 10/609,701, filed on Jun. 30, 2003, now abandoned, which is a continuation of application No. PCT/DK03/00420, filed on Jun. 20, 2003.

(60) Provisional application No. 60/394,778, filed on Jul. 2, 2002.

(30) Foreign Application Priority Data

Jun. 21, 2002 (DK) .................................. 2002 00964

(51) Int. Cl.
A61K 38/16 (2006.01)
C07K 14/00 (2006.01)
(52) U.S. Cl. ................. 514/12; 514/2; 530/384
(58) Field of Classification Search ................ 514/2, 12; 530/384; 435/69.1, 325, 69.6, 183, 254.1, 435/348, 358
See application file for complete search history.

(56) References Cited

U.S. PATENT DOCUMENTS

| 4,055,635 | A | 10/1977 | Green et al. |
| 4,088,538 | A | 5/1978 | Schneider |
| 4,179,337 | A | 12/1979 | Davis et al. |
| 4,385,260 | A | 5/1983 | Watts et al. |
| 4,412,989 | A | 11/1983 | Iwashita et al. |
| 4,414,147 | A | 11/1983 | Klibanov |
| 4,438,253 | A | 3/1984 | Casey et al. |
| 4,496,689 | A | 1/1985 | Mitra |
| 4,565,653 | A | 1/1986 | Ives et al. |
| 4,806,595 | A | 2/1989 | Noishiki et al. |
| 4,826,945 | A | 5/1989 | Cohn et al. |
| 4,847,325 | A | 7/1989 | Shadle et al. |
| 4,879,236 | A | 11/1989 | Smith et al. |
| 4,904,584 | A | 2/1990 | Shaw |
| 4,925,796 | A | 5/1990 | Bergh et al. |
| 5,032,519 | A | 7/1991 | Paulson et al. |
| 5,104,651 | A | 4/1992 | Boone et al. |
| 5,122,614 | A | 6/1992 | Zalipsky |
| 5,147,788 | A | 9/1992 | Page et al. |
| 5,153,265 | A | 10/1992 | Shadle et al. |
| 5,154,924 | A | 10/1992 | Friden |
| 5,166,322 | A | 11/1992 | Shaw et al. |
| 5,169,933 | A | 12/1992 | Anderson et al. |
| 5,182,107 | A | 1/1993 | Friden |
| 5,194,376 | A | 3/1993 | Kang |
| 5,202,413 | A | 4/1993 | Spinu |
| 5,206,344 | A | 4/1993 | Katre et al. |
| 5,219,564 | A | 6/1993 | Zalipsky et al. |
| 5,281,698 | A | 1/1994 | Nitecki |
| 5,324,663 | A | 6/1994 | Lowe |
| 5,324,844 | A | 6/1994 | Zalipsky |
| 5,342,940 | A | 8/1994 | Ono et al. |
| 5,346,696 | A | 9/1994 | Kim et al. |
| 5,352,670 | A | 10/1994 | Venot |
| 5,369,017 | A | 11/1994 | Wong |
| 5,374,541 | A | 12/1994 | Wong et al. |
| 5,374,655 | A | 12/1994 | Kashem et al. |
| 5,405,753 | A | 4/1995 | Brossmer |
| 5,410,016 | A | 4/1995 | Hubbell et al. |
| 5,432,059 | A | 7/1995 | Bean |
| 5,446,090 | A | 8/1995 | Harris |
| 5,492,821 | A | 2/1996 | Callstrom et al. |
| 5,492,841 | A | 2/1996 | Craig |
| 5,527,527 | A | 6/1996 | Friden |
| 5,529,914 | A | 6/1996 | Hubbell et al. |
| 5,545,553 | A | 8/1996 | Gotschlich |
| 5,580,560 | A | 12/1996 | Nicolaisen et al. |
| 5,583,042 | A | 12/1996 | Roth |
| 5,605,793 | A | 2/1997 | Stemmer |
| 5,614,184 | A | 3/1997 | Sytkowski et al. |
| 5,621,039 | A | 4/1997 | Hallahan et al. |
| 5,629,384 | A | 5/1997 | Veronese et al. |
| 5,635,603 | A | 6/1997 | Hansen et al. |
| 5,643,575 | A | 7/1997 | Martinez et al. |

(Continued)

FOREIGN PATENT DOCUMENTS

CA    2397347    8/2001

(Continued)

OTHER PUBLICATIONS

Machine Translation of Japanese Patent 2001-508783, published Jul. 3, 2001.
Machine Translation of Japanese Patent 2003-521930, published Jul. 22, 2003.
Bork et al., *Trends Genet.*, 12(10): 425-427 (1996).
Barrios et al., *J. Mol. Recognit.*, 17(4):332-338 (2004).
Boime et al., *Recent Prog. Horm. Res.*, 54: 271-289 (1999).
Brockhausen et al., *Acta Anatomica*, 161: 36-78 (1998).
Cantin et al., *Am. J Respir. Cell Mol. Biol.*, 27(6): 659-665 (2002).

(Continued)

Primary Examiner — Chih-Min Kam
(74) Attorney, Agent, or Firm — Michael J. Brignati

(57) ABSTRACT

The invention concerns a preparation comprising a plurality of Factor VII polypeptides or Factor VII-related polypeptides, wherein the polypeptides comprise asparagine-linked and/or serine-linked oligosaccharide chains, and wherein at least one oligosaccharide group is covalently attached to at least one polymeric group.

2 Claims, 2 Drawing Sheets

U.S. PATENT DOCUMENTS

| | | | |
|---|---|---|---|
| 5,646,113 A | 7/1997 | Attie et al. |
| 5,672,662 A | 9/1997 | Harris et al. |
| 5,672,683 A | 9/1997 | Friden et al. |
| 5,705,367 A | 1/1998 | Gotschlich |
| 5,716,812 A | 2/1998 | Withers et al. |
| 5,728,554 A | 3/1998 | Bayer et al. |
| 5,770,420 A | 6/1998 | Lowe et al. |
| 5,798,233 A | 8/1998 | Gotschlich |
| 5,811,238 A | 9/1998 | Stemmer et al. |
| 5,824,639 A * | 10/1998 | Berkner ..................... 514/12 |
| 5,824,778 A | 10/1998 | Ishikawa et al. |
| 5,824,864 A | 10/1998 | Fox et al. |
| 5,830,721 A | 11/1998 | Stemmer et al. |
| 5,833,988 A | 11/1998 | Friden |
| 5,834,251 A | 11/1998 | Maras et al. |
| 5,837,458 A | 11/1998 | Minshull et al. |
| 5,849,535 A | 12/1998 | Cunningham et al. |
| 5,858,751 A | 1/1999 | Paulson et al. |
| 5,858,752 A | 1/1999 | Seed et al. |
| 5,861,374 A | 1/1999 | Berkner et al. |
| 5,876,980 A | 3/1999 | DeFrees et al. |
| 5,922,577 A | 7/1999 | Defrees et al. |
| 5,932,462 A | 8/1999 | Harris et al. |
| 5,945,314 A | 8/1999 | Prieto et al. |
| 5,945,322 A | 8/1999 | Gotschlich |
| 5,955,347 A | 9/1999 | Lowe |
| 5,962,294 A | 10/1999 | Paulson et al. |
| 5,969,040 A | 10/1999 | Hallahan et al. |
| 5,977,307 A | 11/1999 | Friden |
| 6,010,999 A | 1/2000 | Daley et al. |
| 6,015,555 A | 1/2000 | Friden |
| 6,030,815 A | 2/2000 | DeFrees et al. |
| 6,037,452 A | 3/2000 | Minamino et al. |
| 6,048,720 A | 4/2000 | Dalborg et al. |
| 6,057,292 A | 5/2000 | Cunningham et al. |
| 6,075,134 A | 6/2000 | Bertozzi et al. |
| 6,087,325 A | 7/2000 | Meers et al. |
| 6,096,512 A | 8/2000 | Elhammer et al. |
| 6,113,906 A | 9/2000 | Greenwald et al. |
| 6,117,651 A | 9/2000 | Schultz et al. |
| 6,166,183 A | 12/2000 | Ishikawa et al. |
| 6,183,738 B1 | 2/2001 | Clark |
| 6,261,805 B1 | 7/2001 | Wood |
| 6,268,193 B1 | 7/2001 | Lowe |
| 6,342,382 B1 | 1/2002 | Gotschlich |
| 6,348,558 B1 | 2/2002 | Harris et al. |
| 6,362,254 B2 | 3/2002 | Harris et al. |
| 6,376,604 B2 | 4/2002 | Kozlowski |
| 6,399,336 B1 | 6/2002 | Paulson et al. |
| 6,399,337 B1 | 6/2002 | Taylor et al. |
| 6,440,703 B1 | 8/2002 | DeFrees |
| 6,458,937 B1 | 10/2002 | Bertozzi et al. |
| 6,465,220 B1 | 10/2002 | Hassan et al. |
| 6,531,121 B2 | 3/2003 | Brines et al. |
| 6,555,346 B1 | 4/2003 | Kretzdorn et al. |
| 6,555,660 B2 | 4/2003 | Nissen et al. |
| 6,586,398 B1 | 7/2003 | Kinstler et al. |
| 6,692,931 B1 | 2/2004 | Reutter et al. |
| 6,693,183 B2 | 2/2004 | Natsuka et al. |
| 6,716,626 B1 | 4/2004 | Itoh et al. |
| 6,743,896 B2 | 6/2004 | Filpula et al. |
| 6,780,624 B2 | 8/2004 | Gotschlich |
| 6,800,740 B1 | 10/2004 | Cunningham et al. |
| 6,949,372 B2 | 9/2005 | Betenbaugh et al. |
| 7,094,530 B1 | 8/2006 | Sasaki et al. |
| 7,125,843 B2 | 10/2006 | DeFrees et al. |
| 7,138,371 B2 | 11/2006 | DeFrees et al. |
| 7,157,277 B2 | 1/2007 | DeFrees et al. |
| 7,173,003 B2 | 2/2007 | DeFrees et al. |
| 7,179,617 B2 | 2/2007 | DeFrees et al. |
| 7,199,223 B2 | 4/2007 | Bossard et al. |
| 7,202,208 B2 | 4/2007 | Papadimitriou |
| 7,214,660 B2 | 5/2007 | DeFrees et al. |
| 7,226,903 B2 | 6/2007 | DeFrees et al. |
| 7,229,962 B2 | 6/2007 | Chung et al. |
| 7,235,638 B2 | 6/2007 | Persson |
| 7,265,084 B2 | 9/2007 | DeFrees et al. |
| 7,265,085 B2 | 9/2007 | DeFrees et al. |
| 7,276,475 B2 | 10/2007 | DeFrees et al. |
| 7,297,511 B2 | 11/2007 | DeFrees et al. |
| 7,304,150 B1 | 12/2007 | Egrie et al. |
| 7,338,933 B2 | 3/2008 | DeFrees et al. |
| 7,368,108 B2 | 5/2008 | DeFrees et al. |
| 7,399,613 B2 | 7/2008 | DeFrees et al. |
| 7,405,198 B2 | 7/2008 | DeFrees et al. |
| 7,416,858 B2 | 8/2008 | DeFrees et al. |
| 7,439,043 B2 | 10/2008 | DeFrees et al. |
| 7,473,680 B2 | 1/2009 | DeFrees et al. |
| 7,691,603 B2 | 4/2010 | DeFrees |
| 7,696,163 B2 | 4/2010 | DeFrees et al. |
| 7,795,210 B2 | 9/2010 | DeFrees et al. |
| 7,803,777 B2 | 9/2010 | DeFrees |
| 7,842,661 B2 | 11/2010 | DeFrees et al. |
| 2002/0016003 A1 | 2/2002 | Saxon et al. |
| 2002/0019342 A1 | 2/2002 | Bayer |
| 2002/0037841 A1 | 3/2002 | Papadimitriou |
| 2002/0115833 A1 | 8/2002 | Burg et al. |
| 2002/0137134 A1 | 9/2002 | Gerngross et al. |
| 2002/0142370 A1 | 10/2002 | Paulson et al. |
| 2002/0150981 A1 | 10/2002 | Canfield |
| 2002/0168323 A1 | 11/2002 | Gonda et al. |
| 2002/0182586 A1 | 12/2002 | Morris et al. |
| 2003/0027257 A1 | 2/2003 | Iatrou et al. |
| 2003/0040037 A1 | 2/2003 | Bayer |
| 2003/0096338 A1 | 5/2003 | Pedersen et al. |
| 2003/0100075 A1 | 5/2003 | Persson et al. |
| 2003/0124645 A1 | 7/2003 | Paulson et al. |
| 2003/0166212 A1 | 9/2003 | Taylor et al. |
| 2003/0166525 A1 | 9/2003 | Hoffmann et al. |
| 2003/0170863 A1 | 9/2003 | Persson et al. |
| 2003/0180835 A1 | 9/2003 | Bayer |
| 2003/0186850 A1 | 10/2003 | Clausen et al. |
| 2003/0195338 A1 | 10/2003 | Chung et al. |
| 2003/0207406 A1 | 11/2003 | Johnson et al. |
| 2004/0043446 A1 | 3/2004 | DeFrees et al. |
| 2004/0063911 A1 | 4/2004 | DeFrees et al. |
| 2004/0077836 A1 | 4/2004 | DeFrees et al. |
| 2004/0082026 A1 | 4/2004 | DeFrees et al. |
| 2004/0102607 A1 | 5/2004 | Danishefsky et al. |
| 2004/0115168 A1 | 6/2004 | DeFrees et al. |
| 2004/0126838 A1 | 7/2004 | DeFrees et al. |
| 2004/0132640 A1 | 7/2004 | DeFrees et al. |
| 2004/0136955 A1 | 7/2004 | Barker |
| 2004/0137557 A1 | 7/2004 | DeFrees et al. |
| 2004/0142856 A1 | 7/2004 | DeFrees et al. |
| 2004/0197875 A1 | 10/2004 | Hauser et al. |
| 2005/0026266 A1 | 2/2005 | Clausen et al. |
| 2005/0031584 A1 | 2/2005 | DeFrees et al. |
| 2005/0064540 A1 | 3/2005 | Defrees et al. |
| 2005/0100982 A1 | 5/2005 | DeFrees et al. |
| 2005/0106658 A1 | 5/2005 | DeFrees et al. |
| 2005/0113565 A1 | 5/2005 | Klausen et al. |
| 2005/0118672 A1 | 6/2005 | DeFrees et al. |
| 2005/0143292 A1 | 6/2005 | DeFrees et al. |
| 2005/0250678 A1 | 11/2005 | DeFrees et al. |
| 2005/0269265 A1 | 12/2005 | DeFrees |
| 2005/0271690 A1 | 12/2005 | Gotschlich |
| 2005/0288490 A1 | 12/2005 | Nakamoto et al. |
| 2006/0024286 A1 | 2/2006 | Glidden |
| 2006/0030521 A1 | 2/2006 | DeFrees et al. |
| 2006/0035224 A1 | 2/2006 | Johansen |
| 2006/0088906 A1 | 4/2006 | DeFrees et al. |
| 2006/0111279 A1 | 5/2006 | DeFrees et al. |
| 2006/0177892 A1 | 8/2006 | De Frees |
| 2006/0246544 A1 | 11/2006 | Kang et al. |
| 2006/0276618 A1 | 12/2006 | DeFrees et al. |
| 2006/0287224 A1 | 12/2006 | DeFrees et al. |
| 2007/0014759 A1 | 1/2007 | DeFrees et al. |
| 2007/0026485 A1 | 2/2007 | DeFrees et al. |
| 2007/0027068 A1 | 2/2007 | DeFrees et al. |
| 2007/0032405 A1 | 2/2007 | DeFrees et al. |
| 2007/0042458 A1 | 2/2007 | DeFrees et al. |
| 2007/0059275 A1 | 3/2007 | DeFrees et al. |
| 2007/0105755 A1 | 5/2007 | DeFrees et al. |
| 2007/0154992 A1 | 7/2007 | DeFrees |
| 2007/0254834 A1 | 11/2007 | DeFrees et al. |
| 2007/0254836 A1 | 11/2007 | Defrees et al. |

| | | | | | |
|---|---|---|---|---|---|
| 2008/0015142 A1 | 1/2008 | DeFrees et al. | WO | WO 90/13540 | 11/1990 |
| 2008/0039373 A1 | 2/2008 | Klausen et al. | WO | WO 91/14697 | 10/1991 |
| 2008/0050772 A1 | 2/2008 | DeFrees et al. | WO | WO 92/15686 | 9/1992 |
| 2008/0070275 A1 | 3/2008 | DeFrees et al. | WO | WO 92/16555 | 10/1992 |
| 2008/0102083 A1 | 5/2008 | DeFrees et al. | WO | WO 92/18135 | 5/1993 |
| 2008/0108557 A1 | 5/2008 | Behrens et al. | WO | WO 93/15189 | 8/1993 |
| 2008/0146494 A1 | 6/2008 | DeFrees et al. | WO | WO 94/04193 | 3/1994 |
| 2008/0146782 A1 | 6/2008 | DeFrees et al. | WO | WO 94/05332 | 3/1994 |
| 2008/0176790 A1 | 7/2008 | DeFrees | WO | WO 94/09027 | 4/1994 |
| 2008/0187955 A1 | 8/2008 | DeFrees et al. | WO | WO 94/15625 | 7/1994 |
| 2008/0200651 A1 | 8/2008 | Ostergaard et al. | WO | WO 94/17039 | 8/1994 |
| 2008/0206808 A1 | 8/2008 | DeFrees et al. | WO | WO 94/18247 | 8/1994 |
| 2008/0206810 A1 | 8/2008 | Johnson et al. | WO | WO 94/27631 | 12/1994 |
| 2008/0207487 A1 | 8/2008 | DeFrees et al. | WO | WO 94/28024 | 12/1994 |
| 2008/0242607 A1 | 10/2008 | DeFrees | WO | WO 95/02421 | 1/1995 |
| 2008/0242846 A1 | 10/2008 | DeFrees et al. | WO | WO 96/10089 | 4/1996 |
| 2008/0248959 A1 | 10/2008 | DeFrees | WO | WO 96/12800 | 5/1996 |
| 2008/0253992 A1 | 10/2008 | DeFrees et al. | WO | WO 96/40731 | 6/1996 |
| 2008/0255026 A1 | 10/2008 | DeFrees et al. | WO | WO 96/21469 | 7/1996 |
| 2008/0255040 A1 | 10/2008 | DeFrees | WO | WO 96/32491 | 10/1996 |
| 2008/0274958 A1 | 11/2008 | DeFrees | WO | WO 96/40881 | 12/1996 |
| 2008/0280818 A1 | 11/2008 | DeFrees | WO | WO 97/05330 | 2/1997 |
| 2008/0300173 A1 | 12/2008 | DeFrees | WO | WO 97/47651 | 12/1997 |
| 2008/0300175 A1 | 12/2008 | DeFrees et al. | WO | WO 98/05363 | 2/1998 |
| 2008/0305991 A1 | 12/2008 | DeFrees et al. | WO | WO 87/05330 | 7/1998 |
| 2008/0305992 A1 | 12/2008 | DeFrees et al. | WO | WO 98/31826 | 7/1998 |
| 2008/0318850 A1 | 12/2008 | DeFrees et al. | WO | WO 98/32466 | 7/1998 |
| 2008/0319183 A1 | 12/2008 | DeFrees et al. | WO | WO 98/51784 | 11/1998 |
| 2009/0028822 A1 | 1/2009 | DeFrees et al. | WO | WO 98/58964 | 12/1998 |
| 2009/0048440 A1 | 2/2009 | Felo et al. | WO | WO 99/00150 | 1/1999 |
| 2009/0053167 A1 | 2/2009 | DeFrees | WO | WO 99/03887 | 1/1999 |
| 2009/0054623 A1 | 2/2009 | DeFrees | WO | WO 99/13063 | 3/1999 |
| 2009/0055942 A1 | 2/2009 | Ostergaard et al. | WO | WO 99/14259 | 3/1999 |
| 2009/0093399 A1 | 4/2009 | DeFrees et al. | WO | WO 99/22764 | 5/1999 |
| 2009/0124544 A1 | 5/2009 | DeFrees | WO | WO 99/34833 | 7/1999 |
| 2009/0137763 A1 | 5/2009 | DeFrees et al. | WO | WO 99/45964 | 9/1999 |
| 2009/0143292 A1 | 6/2009 | Hinderer et al. | WO | WO 99/48515 | 9/1999 |
| 2009/0169509 A1 | 7/2009 | DeFrees et al. | WO | WO99/55376 | 11/1999 |
| 2009/0176967 A1 | 7/2009 | Stennicke | WO | WO 00/23114 | 4/2000 |
| 2009/0203579 A1 | 8/2009 | Defrees et al. | WO | WO 00/26354 | 5/2000 |
| 2009/0227504 A1* | 9/2009 | Klausen et al. ................. 514/12 | WO | WO 00/29558 | 5/2000 |
| 2009/0252720 A1 | 10/2009 | Ostergaard et al. | WO | WO 00/29603 | 5/2000 |
| 2009/0292110 A1 | 11/2009 | Defrees | WO | WO 00/65087 | 11/2000 |
| 2009/0305967 A1 | 12/2009 | Defrees et al. | WO | WO 01/02017 | 1/2001 |
| 2010/0009902 A1 | 1/2010 | Defrees | WO | WO 01/49830 | 7/2001 |
| 2010/0015684 A1 | 1/2010 | Defrees et al. | WO | WO01/58493 | 8/2001 |
| 2010/0028939 A1 | 2/2010 | Behrens et al. | WO | WO 01/58935 | 8/2001 |
| 2010/0029555 A1 | 2/2010 | Tonon et al. | WO | WO 01/60411 | 8/2001 |
| 2010/0035299 A1 | 2/2010 | Defrees et al. | WO | WO 01/76640 | 10/2001 |
| 2010/0041872 A1 | 2/2010 | Defrees et al. | WO | WO 01/83725 | 11/2001 |
| 2010/0048456 A1 | 2/2010 | Defrees et al. | WO | WO 01/88117 | 11/2001 |
| 2010/0056428 A1 | 3/2010 | Behrens | WO | WO 02/02597 | 1/2002 |
| 2010/0075375 A1 | 3/2010 | Defrees et al. | WO | WO 02/02764 | 1/2002 |
| 2010/0081791 A1 | 4/2010 | Defrees et al. | WO | WO 02/13843 | 2/2002 |
| 2010/0113743 A1 | 5/2010 | Defrees et al. | WO | WO 02/13873 | 2/2002 |
| 2010/0120666 A1 | 5/2010 | Zopf et al. | WO | WO 02/29025 | 4/2002 |
| 2010/0174059 A1 | 7/2010 | Defrees et al. | WO | WO 02/053580 | 7/2002 |
| 2010/0210507 A9 | 8/2010 | Defrees et al. | WO | WO 02/074806 | 9/2002 |
| 2010/0286067 A1 | 11/2010 | Defrees | WO | WO 02/002764 | 10/2002 |
| | | | WO | WO 02/077218 | 10/2002 |
| FOREIGN PATENT DOCUMENTS | | | WO | WO 02/092619 | 11/2002 |
| | | | WO | WO 03/017949 | 3/2003 |
| EP | 200421 | 12/1986 | WO | WO 03/031464 | 4/2003 |
| EP | 0585109 | 3/1994 | WO | WO 03/045980 | 6/2003 |
| EP | 0605963 | 7/1994 | WO | WO 03/046150 | 6/2003 |
| EP | 1260582 | 9/1996 | WO | WO 03/093448 | 11/2003 |
| EP | 1428878 | 6/2004 | WO | WO 2004/009838 | 1/2004 |
| EP | 0474313 | 3/2009 | WO | WO 2004/010327 | 1/2004 |
| JP | 59-172425 | 9/1984 | WO | WO 2004/022004 | 3/2004 |
| JP | H03-503759 | 8/1991 | WO | WO 2004/029091 | 4/2004 |
| JP | 6-504678 | 6/1994 | WO | WO 2004/033651 | 4/2004 |
| JP | 9503905 | 4/1997 | WO | WO 2004/046222 | 6/2004 |
| JP | 2001-508783 | 7/2001 | WO | WO 2004/083258 | 9/2004 |
| JP | 2003-521930 | 7/2003 | WO | WO 2004/083259 | 9/2004 |
| WO | WO 87/00056 | 1/1987 | WO | WO 2004/091499 | 10/2004 |
| WO | WO 89/06546 | 7/1989 | WO | WO 2004/096148 | 11/2004 |
| WO | WO 89/10134 | 11/1989 | WO | WO 2004/099231 | 11/2004 |
| WO | WO 90/07572 | 7/1990 | WO | WO 2004/103275 | 12/2004 |
| WO | WO 90/08164 | 7/1990 | WO | WO 2005/012484 | 2/2005 |
| WO | WO 90/08823 | 8/1990 | | | |

| | | |
|---|---|---|
| WO | WO 2005/025606 | 3/2005 |
| WO | WO 2005/051327 | 6/2005 |
| WO | WO 2005/055946 | 6/2005 |
| WO | WO 2005/056760 | 6/2005 |
| WO | WO 2005/067601 | 7/2005 |
| WO | WO 2005/070138 | 8/2005 |
| WO | WO 2005/072371 | 8/2005 |
| WO | WO 2005/091944 | 10/2005 |
| WO | WO 2005/121331 | 12/2005 |
| WO | WO 2006/010143 | 1/2006 |
| WO | WO 2006/014349 | 2/2006 |
| WO | WO 2006/014466 | 2/2006 |
| WO | WO 2006/020372 | 2/2006 |
| WO | WO 06/031811 | 3/2006 |
| WO | WO 2006/050247 | 5/2006 |
| WO | WO 2006/074279 | 7/2006 |
| WO | WO 2006/074467 | 7/2006 |
| WO | WO 2006/078645 | 7/2006 |
| WO | WO 2006/105426 | 10/2006 |
| WO | WO 2006/121569 | 11/2006 |
| WO | WO 2006/127910 | 11/2006 |
| WO | WO 2007/022512 | 2/2007 |
| WO | WO 2007/056191 | 5/2007 |
| WO | WO 2008/011633 | 1/2008 |
| WO | WO 2008/057683 | 5/2008 |
| WO | WO 2008/060780 | 5/2008 |
| WO | WO 2008/073620 | 6/2008 |
| WO | WO 2008/124406 | 10/2008 |
| WO | WO 2008/151258 | 12/2008 |
| WO | WO 2008/154639 | 12/2008 |
| WO | WO 2009/089396 | 7/2009 |

OTHER PUBLICATIONS

Chang, et al., *Biochemistry*, 38(34): 10940-10948 (1999).
Cohn el al., *J. Biomed. Maier. Res,.* 22(11): 993-1009 (1988).
Dickinson et al., Proc. Natl. Acad. Sci. USA, 93: 14379-14384 (1996).
Edge et al., *Anal. Biochem.*, 118(1): 131-137 (1981).
Felix et al., *J Peptide Res.*, 63: 85-90 (2004).
Ge et al., *J. Biol. Chem.*, 272(34): 21357-21363 (1997).
Gervais et al., *Glycobiology*, 13(3): 179-189 (2003).
Goodson et al., Bio/Technology, 4: 343-346 (1990).
Grabenhorst et al., *J. Biol. Chem.*, 274(51): 36107-36116 (1999).
Gross et al., *Biochemistry*, 28(18): 7386-7392 (1989).
Hassan et al., *Carbohydrates in Chemistry and Biology*, Part II, 3: 273-292 (2000).
Herscovics et al., *FASEB J.*, 7(6): 540-550 (1993).
Kajihara et al., *Carbohydrate Research*, 315: 137-141 (1999).
Katre et al., *Proc. Natl. Acad. Sci. USA*, 84(6): 1487-1491 (1987).
Kawasaki et al., *Anal. Biochem.*, 285: 82-91 (2000).
Keana et al., *J. Org. Chem.*, 55(11): 3640-3647 (1990).
Kobayashi et al., *Eur. J. Nucl. Med.*, 27(9):1334-1339 (2000).
Kogan, Timothy P., Synthetic Communications, 22(16): 2417-2424 (1992).
Kornfeld et al., *Ann. Rev. Biochem.*, 54: 631-664 (1985).
Kukuruzinska et al., *Proc. Natl. Acad. Sci. USA*, 84(8): 2145-2149 (1987).
Langer, Science, 249(4976): 1527-1533 (1990).
Legault et al., *J. Biol. Chem.*, 270(36): 20987-20996 (1995).
Lin et al., *Proc. Natl. Acad. Sci. USA*, 82: 7580-7584 (1985).
Meyntal-Salles et al., *J. Bioteehnol.*, 46(1): 1-14 (1996).
Min et al., *Endocr. J.*, 43(5): 585-593 (1996).
Mizuguchi et al., Throtnb. Haetnost., abstract 1474, p. 466, supplement Aug. 1999.
Muller et al., *J. Biol. Chem.*, 272(40): 24780-24793 (1997).
Muller et al., *J. Biol. Chem.*, 274(26): 18165-18172 (1999).
Nucci et al., Advanced Drug Delivery Reviews, 6: 133-151 (1991).
Orlean, "vol. III: The Molecular and Cellular Biology of the Yeast Saccharomyces: Cell Cycle and Cell Biology", in *Biogenesis of Yeast Wall and Surface Components*, Chapter 3, pp. 229-362, Cold Spring Harbor Laboratory Press (1997).
Rotondaro et al., *Mol. Biotech.*, 11: 117-128 (1999).
Rudikoff et al., *Proc. Natl. Acad. Sci. USA*, 79(6):1979-1983 (1982).
Sasaki et al., *J. Biol. Chem.*, 262(25): 12059-12076 (1987).
Sasaki et al., *J.Biol. Chem.*, 269: 14730-14737 (1994).
Seely et al., *J. Chromatog.*, 908: 235-241 (2001).
Seitz, *Chembiochem.*, 1(4): 214-246 (2000).
Shen et al., *Biochem. Biophys. Res. Commun.*, 102(3): 1048-1054 (1981).
Shinkai et al., *Prot. Exp. Purif.*, 10: 379-385 (1997).
Snider et al., *J. Chromatogr.*, A 599(1-2): 141-155 (1992).
Sojar et al., *Arch. Biochem. Biophys.*, 259(1): 52-57 (1987).
Srinivasachar et al., *Biochemistry*, 28(6): 2501-2509 (1989).
Stemmer, *Nature*, 370(6488): 389-391 (1994).
Stemmer, *Proc. Natl. Acad. Sci. USA*, 91(22): 10747-10751 (1994).
Strausberg et al., *Proc Natl Acad Sci USA*, 99(26): 16899-16903 (2002).
Takeya et al., Journal of Biological Chemistry, 263(29): 14868-14877 (1988).
Taniguchi et al., *Proteomics*, 1(2): 239-247 (2001).
Ten Hagen et al., *J. Biol. Chem.*, 274(39): 27867-27874 (1999).
Tsunoda et al., *J. Pharmacol. Exp. Ther.*, 209(1): 368-372 (1999).
Urdal et al, *J. Chromatogr.*, 296: 171-179 (1984).
Van Reis et al., *Biotechnol. Bioeng.*, 38(4): 413-422 (1991).
Vitetta et al., *Science*, 313: 308-309 (2006).
White et al., *J. Biol. Chem.*, 270(41): 24156-24165 (1995).
Witte et al., *J Am. Chem. Soc.*, 119(9): 2114-2118 (1997).
Witte et al., *Cancer and Metastasis Rev.*, 17: 155-161 (1998).
Wong et al., *J. Org. Chem.*, 47(27): 5416 5418 (1982).
Wu et al., *J. Drug Target.*, 10(3): 239-245 (2002).
Yamada et al., *Biochemistry*, 20(1 7): 4836-4842 (1981).
Younes et al., *J. Biomed. Mater. Res.*, 21(11): 1301-1316 (1987).
Zarling et al., *J. Immunol.*, 124(2): 913-920 (1980).
Harris et al. (eds.), "Poly(ethylene glycol): Chemistry and Biological Applications," ACS Symposium Series, vol. 680, American Chemical Society (1997) (includes 28 abstracts listed below).
Abstract of Zalipsky et al., *Introduction to Chemistry and Biological Applications of Poly(ethylene glycol)* as published in Harris et al. (eds.), "Poly(ethylene glycol): Chemistry and Biological Applications," ACS Symposium Series, vol. 680, American Chemical Society (1997).
Abstract of Karlstrom et al., *Theory of Poly(ethylene glycol) in Solution* as published in Harris et al. (eds.), "Poly(ethylene glycol): Chemistry and Biological Applications," ACS Symposium Series, vol. 680, American Chemical Society (1997).
Abstract of Lasic, *The Conformation of Polymers at Interfaces* as published in Harris et al. (eds.), "Poly(ethylene glycol): Chemistry and Biological Applications," ACS Symposium Series, vol. 680, American Chemical Society (1997).
Abstract of Working et al., *Safety of Poly(ethylene glycol) and Poly(ethylene glycol) Derivatives* as published in Harris et al. (eds.), "Poly(ethylene glycol): Chemistry and Biological Applications," ACS Symposium Series, vol. 680, American Chemical Society (1997).
Abstract of Woodle et al., *Poly (ethylene glycol)-Grafted Liposome Therapeutics* as published in Harris et al. (eds.), "Poly(ethylene glycol): Chemistry and Biological Applications," ACS Symposium Series, vol. 680, American Chemical Society (1997).
Abstract of Okumura et al., *Poly(ethylene oxide)-Bearing Lipids and Interaction of Functionalized Liposomes with Intact Cells* as published in Harris et al. (eds.), "Poly(ethylene glycol): Chemistry and Biological Applications," ACS Symposium Series, vol. 680, American Chemical Society (1997).
Abstract of La et al., *Poly(ethylene glycol)-Based Micelles for Drug Delivery* as published in Harris et al. (eds.), "Poly(ethylene glycol): Chemistry and Biological Applications," ACS Symposium Series, vol. 680, American Chemical Society (1997).
Abstract of Mabrouk, *The Use of Poly(ethylene glycol)-Enzymes in Nonaqueous Enzymology* as published in Harris et al. (eds.), "Poly(ethylene glycol): Chemistry and Biological Applications," ACS Symposium Series, vol. 680, American Chemical Society (1997).
Abstract of Panza et al., *Incorporation of Poly(ethylene glycol)-Proteins into Polymers* as published in Harris et al. (eds.), "Poly(ethylene glycol): Chemistry and Biological Applications," ACS Symposium Series, vol. 680, American Chemical Society (1997).
Abstract of Hershfield, *Biochemistry and Immunology of Poly(ethylene glycol)-Modified Adenosine Deaminase (PEG-ADA)* as published in Harris et al. (eds.), "Poly(ethylene glycol): Chemistry and Biological Applications," ACS Symposium Series, vol. 680, American Chemical Society (1997).
Abstract of Sherman et al., *Conjugation of High-Molecular Weight Poly(ethylene glycol) to Cytokines: Granulocyte-Macrophage Colony-Stimulating Factors as Model Substrates* as published in Harris et al. (eds.), "Poly(ethylene glycol): Chemistry and Biological Applications," ACS Symposium Series, vol. 680, American Chemical Society (1997).
Abstract of Olson et al., *Preparation and Characterization of Poly(ethylene glycol)ylated Human Growth Hormone Antagonist* as published in Harris et al. (eds.), "Poly(ethylene glycol): Chemistry and Biological Applications," ACS Symposium Series, vol. 680, American Chemical Society (1997).
Abstract of Verenose et al., *New Synthetic Polymers for Enzyme and Liposome Modification* as published in Harris et al. (eds.), "Poly(ethylene glycol): Chemistry and Biological Applications," ACS Symposium Series, vol. 680, American Chemical Society (1997).
Abstract of Topchieva, *Covalent and Noncovalent Adducts of Proteins with Water-Soluble Poly(alkylene oxides)* as published in Harris et al. (eds.), "Poly(ethylene glycol): Chemistry and Biological Applications," ACS Symposium Series, vol. 680, American Chemical Society (1997).
Abstract of Monkarsh et al., *Isolation of Positional Isomers of Monopoly(ethylene glycol)ylated Inteiferon/a-2a and the Determination of Their Biochemical and Biological Characteristics* as published in Harris et al. (eds.), "Poly(ethylene glycol): Chemistry and Biological Applications," ACS Symposium Series, vol. 680, American Chemical Society (1997).
Abstract of Jaschke, *Oligonucleotide-Poly(ethylene glycol) Conjugates: Synthesis, Properties, and Applications* as published in Harris et al. (eds.), "Poly(ethylene glycol): Chemistry and Biological Applications," ACS Symposium Series, vol. 680, American Chemical Society (1997).
Abstract of Barany et al., *Poly(ethylene glycol)-Containing Supports for Solid-Phase Synthesis of Peptides and Combinatorial Organic Libraries* as published in Harris et al. (eds.), "Poly(ethylene glycol): Chemistry and Biological Applications," ACS Symposium Series, vol. 680, American Chemical Society (1997).
Abstract of Ouchi, *Design of Antitumor Agent-Terminated Pol(ethylene glycol) Conjugate as Macromolecular Prodrug* as published in Harris et al. (eds.), "Poly(ethylene glycol): Chemistry and Biological Applications," ACS Symposium Series, vol. 680, American Chemical Society (1997).
Abstract of Schacht et al., *Poly(ethylene glycol)-Grafted Polymers as Drug Carriers* as published in Harris et al. (eds.), "Poly(ethylene glycol): Chemistry and Biological Applications," ACS Symposium Series, vol. 680, American Chemical Society (1997).
Abstract of Zalipsky et al., *Hydrazide Derivatives of Poly(ethylene glycol) and Their Bioconjugates* as published in Harris et al. (eds.), "Poly(ethylene glycol): Chemistry and Biological Applications," ACS Symposium Series, vol. 680, American Chemical Society (1997).
Abstract of Sofia et al., *Protein Adsorption of Poly(ethylene oxide)-Grafted Silicon Surfaces* as published in Harris et al. (eds.), "Poly(ethylene glycol): Chemistry and Biological Applications," ACS Symposium Series, vol. 680, American Chemical Society (1997).
Abstract of Mrksich et al., *Using Self-Assembled Monolayers That Present Oligo(ethylene glycol) Groups to Control the Interactions of Proteins with Surfaces* as published in Harris et al. (eds.), "Poly(ethylene glycol): Chemistry and Biological Applications," ACS Symposium Series, vol. 680, American Chemical Society (1997).
Abstract of Emoto et al., *Electrokinetic Analysis of Poly(ethylene glycol) Coating Chemistry* as published in Harris et al. (eds.), "Poly(ethylene glycol): Chemistry and Biological Applications," ACS Symposium Series, vol. 680, American Chemical Society (1997).
Abstract of Caldwell, *Surface Modifications with Adsorbed Poly(ethylene oxide)-Based Block Copolymers Physical Characteristics and Biological Use* as published in Harris et al. (eds.), "Poly(ethylene glycol): Chemistry and Biological Applications," ACS Symposium Series, vol. 680, American Chemical Society (1997).
Abstract of Rhee et al., *In vivo Stability of Poly(ethylene glycol)-Collagen Composites* as published in Harris et al. (eds.), "Poly(ethylene glycol): Chemistry and Biological Applications," ACS Symposium Series, vol. 680, American Chemical Society (1997).
Abstract of Chen et al., *Temperature-Induced Gelation Pluronic-g-Poly(acrylic acid) Graft Copolymers for Prolonged Drug Delivery to the Eye* as published in Harris et al. (eds.), "Poly(ethylene glycol): Chemistry and Biological Applications," ACS Symposium Series, vol. 680, American Chemical Society (1997).
Abstract of Zhao et al., *Novel Degradable Poly(ethylene glycol) Esters for Drug Delivery* as published in Harris et al. (eds.), "Poly(ethylene glycol): Chemistry and Biological Applications," ACS Symposium Series, vol. 680, American Chemical Society (1997).
Alam et al., 1998, Journal of Biotechnology. 65:183-190.
Bedard et al., 1994, Cytotechnology 15:129-138.
Bennett et al., 1998, J. Biol. Chem. 273:30472-30481.
Bennett et al., 1999, FEBS Letters 460:226-230.
Bork et al., (1996) Trends in Genetics 12 (10):425-427.
Brenner (1999) Trends in Genetics 15(4) 132-133.
Doerks et al., (1998) Trends in Genetics 14(6):248-250.
Fritz et al., 2004, PNAS 101(43):15307-15312.
Fritz et al., 2006, J. Biol. Chem. 281(13):8613-8619.
Gilbert et al., 1996, Cytotechnology 22:211-216.
Hagen et al., 1999, J. Biol. Chem. 274:27867-27874.
Hagen et al., 1999, J. Biol. Chem. 274:6797-6803.
Hagen et al., 2001, J. Biol. Chem. 276:17395-17404.
Hassan et al., 2000, J. Biol. Chem. 275:38197-38205.
Hink et al., 1991, Biotechnology Progress 7:9-14.
Ikonomou et al., 1991, In Vitro Cell. Dev. Biol.-Animal 37:549-559.
Inlow et al., 1989, J. Tissue Culture Meth. 12:13-16.
Lau et al. (1999) Journal of Biotechnology 75:105-115.
Licari P. et al., 1992, Biotechnology and Bioengineering 39(4):432-441.
Licari P. et al., 1992, Biotechnology and Bioengineering 39(9):932-944.
Ngo et al. (1994) "The Protein Folding Problem and Tertiary Structure Prediction, and the Levinthal Paradox" pp. 433-440 and 492-495.
Reis et al.,1991, Biotechnology and Bioengineering 38:413-422.
Sandberg et al., 2000, Seminars in Hematology 38(2):4-12.
Schlaeger, E., 1996, Cytotechnology 20:57-70.
Schwientek et al., 2002, Biol. Chem. 277:22623-22638.
Skolnick et al. (2000) Trends in Biotech. 18(1):34-39.
Smith et al. (1997) Nature Biotechnology 15:1222-1223.
Tenno et al., 2002, Biochemistry 29(37):8509-8517.
Wells (1990) Biochemistry 29(37):8509-8517.
Final Rejection mailed on Nov. 20, 2009 in U.S. Appl. No. 11/580,669, filed Oct. 13, 2006 by DeFrees et al.
Abeijon et al., 1986, J. Biol. Chem. 261(24):11374-11377.
Abuchowski et al., 1977, J. Biol. Chem. 252:3578-3581.
Abuchowski et al., 1977, J. Biol. Chem. 252:3582-3586.
Abuchowski et al., 1984, Cancer Biochem. Biophys. 7:175-186.
Ailor et al., 2000, Glycobiology 10:837-847.
Allegre et al., 2006, J. Membrane Science 269:109-117.
Altmann et al., 1999, Glycoconjugate J. 16:109-123.
Aplin et al., 1981, CRC Crit Rev. Biochem. 259-306.
Beauchamp et al., 1983, Anal Biochem.131:25-33.
Berger et al., 1988, Blood 71:1641-1647.
Berg-Fassman et al. 1993, J. Biol. Chem. 268:14861-14866.
Bhadra et al., 2002, Pharmazie 57:5-29.
Bhatia et al., 1989, Anal. Biochem. 178:408-413.
Bickel et al., 2001, Adv. Drug Deliv. Rev. 46:247-279.
Bjoern, et al., J. Biol. Chem., 266(17):11051-11057, 1991.
Boccu et al., 1983, Z. Naturforsch 38C:94-99.
1995, Endocrinology 136:2635-2640, Bishop et al.
Boissel et al., 1993, J. Biol. Chem. 268:15983-15993.
Bouizar et al., 1986, Eur. J. Biochem. 155:141-147.
Boyd et al., 1995, Mol. Immunol. 32:1311-1318.
Browning et al., 1989, J. Immunol. 143:1859-1867.
Bückmann et al., 1981, Makromol. Chem.182:1379-1384.
Burns et al., 2002, Blood 99:4400-4405.
Busterbosch et al., 1996, Eur. J. Biochem. 237:344-349.
Butnev et al., 1998, Biology of Reproduction 58:458-469.
Byun et al., 1992, ASAIO Journal M649-M653.
Casares et al., 2001, Nature Biotech 19:142-147.

Chaffee et al., 1992, J. Clin. Invest 89:1643-1651.
Charter et al., 2000, Glycobiology 10:1049-1056.
Chem et al., 1991, Eur. J. Biochem. 202:225-229.
Chiba et al., 1995, Biochem J. 308:405-409.
Chrisey et al., 1996, Nucleic Acids Res. 24:3031-3039.
Clark, et al., 1996, J. Biol. Chem,271(36)21969-21977.
Cointe, et al., 2000, Glycobiology, 10(5):511-519.
Conradt et al., 1987, J. Biol. Chem. 262:14600-14605.
Cope et al., 1991, Molecular Microbiology 5(5):1113-1124.
Copeland, Robert A., 2000, Enzymes, Second Edition, 146-150.
Crout et al., 1998, Curr. Opin. Chem. Biol. 2:98-111.
DeFrees, 2006, Glycobiology 16:833-843.
Delgado et al., 1992, Critical Reviews in Therapeutic 9:249-304.
Delgaldo et al., 1990, Biotechnol. Appl. Biochem. 12:119-128.
Detty et al., 1982, J. Org. Chem. 47:5416-5418.
Douglas, et al., 1991, J. Am. Chem. Soc., 113:5095-5097.
Dunn et al., 1991, Eds. Polymeric Drugs and Drug Delivery Systems, ACS Symposium Series vol. 469, American Chemical Society, Washington D.C.
Durieux, et al., 2001, Tetrahedron Letters, 42:2297-2299.
Dwek et al., 1995, J. Anat. 187:279-292.
Eavarone et al., 2000, J. Biomed Mater. Res. 51:10-14.
Fan et al., 1997, J. Biol. Chem. 272(43):27058-27064.
Fibi et al., 1995, Cells Blood 85:1229-1236.
Fischer et al., 1998, Thrombosis Research 89:147-150.
Flynn et al., 2000, Curr. Opin. Oncol. 12:574-581.
Garnett et al., 2002, Advanced Drug Delivery Reviews 53:171-216.
Gatot, et al., 1998, J. Biol. Chem., 273(21):12870-12880.
Gillis et al., 1988, Behring Inst. Mitt. August 83:1-7.
Ginns, Dr. Edward, PEG Glucocerebrosidase, Internet page from www.gaucher.org.uk/peg2.prg, printed Jun. 21, 2002.
Gotschlich, Emil C., 1994, J. Exp. Med., Coden: Jemeav; ISSN: 0022-1007, 180(6):2181-90.
Grabenhorst, et al., 1993, Euro. J. Biochem., 215:189-197.
Kasina et al., 1998 Bioconjugate Chem., 9:108-117.
Katre et al., 1987, Proc. Natl. Acad. Sci. U.S.A. 84:1487-1491.
Keppler et al., 2001, Glycobiology 11:11R-18R.
Kitamura et al., 1990, Biochem. Biophys. Res. Commun. 28:1387-1394.
Kitamura et al., 1991, Cancer Res. 51:4310-4315.
Kodama et al., 1993, Tetrahedron Lett. 34:6419-6422.
Koeller et al., 2000, Nature Biotechnology 18: 835-841.
Koeller et al., 2001, Nature, 409:232-240.
Koide et al., 1983, Biochem Biophys. Res. Commun. 111:659-667.
Kreitmann 2001, Current Pharmaceutical Biotechnology 2:313-325.
Kuhn, et al., 1995, J. Biol. Chem. 270(49):29493-29497.
Lai et al, 1986, J. Biol. Chem. 261:3116-3121.
Lee-Huang et al., 1984, Proc. Natl. Acad. Sci. U.S.A. 81:2708-2712.
Lee et al., 1989, Biochemistry 28:1856-1861.
Leung, S., 1995, J. Immunology, 154:5919-5926.
Li et al., 2002, Trends in Pharmacological Sciences 23:206-209.
Li et al., 2002, Medicinal Research Reviews 22:225-250.
Liu et al., 1996, Chem. Eur. J. 2:1359-1362.
Long et al., 2006, Experimental Hematology 34:697-704.
Lord et al., 2001, Clin. Cancer Res. 7:2085-2090.
Lougheed et al., 1999, J. Biol. Chem. 274:37717-37722.
Luckow et al., 1993, Curr. Opin. Biotechnol 4:564-572.
Lund et al., 1995, FASEB J. 9:115-119.
Lund et al., 1996, J. Immunol. 157:4963-4969.
Mahal et al., 1997, Science 276:1125-1128.
Maranga et al., 2003, Biotechnology and Bioengineering 84(2):245-253.
Maras et al., 2000, Molecular cloning and enzymatic characterization of a Trichoderma reesei , 2-α-D-mannosidase, 77:255-263.
Miller et al., 1993, Curr. Opin. Genet. Dev. 3:97-101.
Min et al., 1996, Endocr. J. 43:585-593.
Mistry et al., 1996, Lancet 348:1555-1559.
Morimoto et al., 1996, Glycoconjugate J. 13:1013-1020.
NCBI—Accession No. NCAA26095 (2 pgs.), Nov. 2006.
NCBI—Accession No. NP_999299 (2 pgs.), Sep. 2007.
Accession No. NP 058697 (3 pgs.), Jun. 2007.
NCBI Database hits for erythropoietin protein sequences (3 pgs.).
Nilsson et al., 1984, Methods Enzymol. 104:56-69.

O'Connell et al., 1992, J. Biol. Chem. 267:25010-25018.
Oetke et al, 2002, J. Biol. Chem 277(8):6688-6695.
Olson et al., 1999, J. Biol. Chem. 274:29889-29896.
Palacpac et al., 1999, PNAS USA 96:4692-4697.
Park et al., 1986, J. Biol Chem. 261:205-210.
Paulson et al., 1997, J. Biol. Chem. 252:8624-8628.
Plummer et al., 1995, J. Biol. Chem. 270(22):13192-13196.
PNGase-F Amidase Sequence from F. Meningosepticum (Registry Nos. 128688-70-0).
PNGase-F Amidase Sequence from F. Meningosepticum (Registry Nos. 128688-71-1).
Pyatak et al., 1980, Res. Commun. Chem. Pathol Pharmacol 29:113-127.
Rabouille et al., 1999, J. Cell. Biol. 112:3319-3330.
Reff et al., 2002, Cancer Control 9:152-166.
Rosenthal, et al., 1994, Methods Enzymol. 235:253-285.
Sadler et al., 1982, Methods in Enzymology 83:458-514.
Saneyoshi et al., 2001, Biology of Reproduction 65:1686-1690.
Saxon et al., 2000, Science 287:2007-2010.
Schwientek et al., 1994, Gene 145:299-303.
Scouten 1987, Methods in Enzymology 135:30-65.
Shah et al., 1996, J. Pharm. Sci. 85:1306-1311.
Shapiro et al., 2005, B. Biochemistry 105:518-525.
Singh et al., 1996, Chem. Commun. 1996:993-994.
Sinha et al., 1980, Infection and Immunity 29(3):914-925.
Song et al., 2002, J. Pharmacol. Exp. Ther. 301:605-610.
Srinivasachar et al., 1989, Biochemistry 28:2501-2509.
Stephens et al., 1983, European J. of Biochem., 135(3):519-27.
Stephens et al., 1983, European J. of Biochem., 133(3):481-9.
Stephens et al., 1983, European J. of Biochem., 133(1):155-62.
Takane et al., 2000, J. Pharmacology and Experimental Therapeutics 294:746-752.
Takeda et al., 1995, Trends Biochem. Sci. 20:367-371.
Takeuchi, et al., 1990, The Journal of Biological Chemistry, 265(21): 12127-12130.
Tanner et al., 1987, Biochim. Biophys. Acta., 906:81-91.
Taylor et al., 1991, Protein Immobilization Fundamentals and Applications, Manual.
Thotakura et al., 1987, Meth Enzymol 138: 350-359.
Tsuboi et al., 2000 Archives of Biochemistry and Biophysics 374:100-106.
Tuddenham, E., 2002, Nature 419:23-24.
Udenfriend et al., 1995, Ann. Rev. Biochem. 64:563-591.
Ulloa-Aguirre et al., 1999, Role of Glycosylation in Function of Follicle-Stimulating Hormone, Endocrine 11:205-215.
Uludag et al., 2002, Biotechnol. Prog. 18:604-611.
Urdal et al, 1984, J. Chromatog, 296:171-179.
Van Berkel et al., 1996, Biochem J. 319:117-122.
Veronese et al., 1985, Appl. Biochem. Biotech. 11:141-152.
Vocadlo et al., 2000, In Carbohydrate Chemistry and Biology, vol. 2.
Vyas et al., 2001, Crit. Rev. Ther. Drug Carrier Syst. 18:1-76.
Wang et al., 1996, Tetrahedron Lett. 37:1975-1978.
Wang, M., 1998, Protein Engineering 11(12):1277-1283.
Wellhoner et al., 1991, J. Biol. Chem. 226:4309-4314.
Witte K. et al., 1997, J. Am. Chem. Soc. 119:2114-2118.
Woghiren et al., 1993, Bioconjugate Chem. 4:314-318.
Wong et al., 1992, Enzyme Microb.Technol. 14:866-874.
Wong et al., 1996, Biotechnology and Bioengineering 49:659-666.
Woods et al., 1989, Eur. J. Cell. Biol. 50:132-143.
Wright et al., 1998, J. Immunol. 160:3393-3402.
Wu et al., 2002, J. Drug targeting 10:239-245.
Xing et al., 1998, Biochem. J. 336:667-673.
Yamamoto et al., 1998, Carbohydr. Res. 305:415-422.
Yarema et al., 1998, J. Biol. Chem. 47:31168-31179.
Yoshida et al., 1999, Glycobiology 9:53-58.
Yoshitake et al., 1985, Biochemistry 24:3736-3750.
Zalipsky 1995, Bioconjugate Chem. 6:150-165.
Zalipsky et al., 1992, Poly (ethylene glycol) Chemistry: Biotechnical and Biomedical Applications 347-370.
Zheng et al., 1999, Biotechnology and Bioengineering 65(5):600-604.
Zhou, et al., 1994, Mol. Microbiol. 14(4):609-618.

Non Final Office Action mailed Aug. 21, 2008 for U.S. Appl. No. 10/411,044, filed Apr. 9, 2003 by Shawn DeFrees.
Final Office Action mailed May 11, 2009 for U.S. Appl. No. 10/411,044, filed Apr. 9, 2003 by Shawn DeFrees.
Notice of Allowance mailed May 24, 2010 for U.S. Appl. No. 10/411,044, filed Apr. 9, 2003 by Shawn DeFrees.
Non Final Office Action mailed Jun. 29, 2005 for U.S. Appl. No. 10/287,994, filed Nov. 5, 2002 by Shawn DeFrees.
Final Office Action mailed Nov. 15, 2005 for U.S. Appl. No. 10/287,994, filed Nov. 5, 2002 by Shawn DeFrees.
Notice of Allowance mailed Jan. 12, 2006 for U.S. Appl. No. 10/287,994, filed Nov. 5, 2002 by Shawn DeFrees.
Non Final Office Action mailed Apr. 27, 2007 for U.S. Appl. No. 11/183,205, filed Jul. 15, 2005 by Shawn DeFrees.
Non Final Office Action mailed Oct. 16, 2007 for U.S. Appl. No. 11/183,205, filed Jul. 15, 2005 by Shawn DeFrees.
Notice of Allowance mailed Jun. 9, 2008 for U.S. Appl. No. 11/183,205, filed Jul. 15, 2005 by Shawn DeFrees.
Notice of Allowance mailed May 17, 2007 for U.S. Appl. No. 11/404,266, filed Apr. 12, 2006 by Shawn DeFrees.
Non Final Office Action mailed Aug. 26, 2008 for U.S. Appl. No. 11/580,669, filed Oct. 13, 2006 by Shawn DeFrees.
Non Final Office Action mailed Mar. 4, 2009 for U.S. Appl. No. 11/580,669, filed Oct. 13, 2006 by Shawn DeFrees.
Final Office Action mailed Nov. 20, 2009 for U.S. Appl. No. 11/580,669, filed Oct. 13, 2006 by Shawn DeFrees.
Non Final Office Action mailed Dec. 16, 2003 for U.S. Appl. No. 10/109,498, filed Mar. 22, 2002 by Egon Persson.
Non Final Office Action mailed Jun. 9, 2005 for U.S. Appl. No. 10/109,498, filed Mar. 22, 2002 by Egon Persson.
Final Office Action mailed Jul. 28, 2006 for U.S. Appl. No. 10/109,498, filed Mar. 22, 2002 by Egon Persson.
Notice of Allowance mailed Feb. 23, 2007 for U.S. Appl. No. 10/109,498, filed Mar. 22, 2002 by Egon Persson.
Grodberg et al., 1993, Eur. J. Biochem. 218:597-601.
Gross, H.J., 1992, Eur. J. Biochem. 203(1-2):269-275.
Hall et al., 2001, Methods in Molecular Biology 166:139-154.
Haneda et al., Carbohydr. Res. 292:61-70, (1996).
Hang et al., 2001, J. Am. Chem. Soc. 123:1242-1243.
Harris et al, Abstracts of Papers of the American Chemical Society, 1991, V201, APR, P 64-Poly, p. 154-155.
Harris et al, 2003, Nature Reviews Drug Discovery, 2:214-221.
Harris, 1985, Macronol. Chem. Phys. C25: 325-373.
Hayes et al, 1993, J. Biol. Chem. 268(22): 16170-16178.
Hellstrom et al., 2001, Methods in Molecular Biology 166:3-16.
Hermanson et al., 1992, Immobilized Affinity Ligand Techniques, Academic Press.
Hermanson, 1996, Bioconjugate Techniques, Academic Press, San Diego.
Hermentin, et al., 1996, Glycobiology 6(2):217-230.
Hills et al., 2002, American Biotechnology Laboratory, 20(11):30.
Hollister et al., 2001, Glycobiology 11:1-19.
Hounsell et al., 1996, Glycoconi. J. 13:19-26.
Ichikawa et al., 1992, J. Am. Chem. Soc. 114:9283-9298.
Inoue et al., 1995, Biotechnology Annual Review 1:297-313.
Ito et al., 1993, Pure & Appl. Chem. 65(4):753-762.
Jackson et al., 1987, Anal. Biochem.165:114-127.
Jarvis et al., 1998, Curr. Opin. Biotechnol. 9:528-533.
Joppich et al., 1979, Makromol Chem. 180:1381-1384.
Joshi et al., 1990, J. Biol. Chem. 265:14518-14525.
Jung et al., 1983, Biochem. Biophys. Acta, 761:152-162.
Kalsner et al., 1995, Glycoconj. J. 12:360-370.
U.S. Appl. No. 11/580,669, filed on Oct. 13, 2006, Defrees.
Adelhorst et al., J. Biol. Chem., vol. 269(9), pp. 6275-6278 (1994).
Bishop et al., Endocrinology 136:2635-2640 (1995).
Bork, 2000, "Powers and Pitfalls in Sequence Analysis: The 70% Hurdle," Genome Research 10:398-400.
Brockhausen et al., Acta Anat. 161:36-78(1998).
Broun et al., Science, vol. 282(5392), pp. 1315-1317 (1998).
Costa et al. J. Bol. Chem., vol. 272(17), pp. 11613-11621 (1997).
Culajay et al., "Thermodynamic Characterization of Mutants of Human Fibroblast Growth Factor 1 With an Increased Physiological Half-Life," Biochemistry, vol. 39, pp. 7153-7158 (2000).

De Vries et al., J. Bol. Chem, vol. 270(15), pp. 8712-8722 (1995).
De Vries et al., Glycobiology, vol. 7(7), pp. 921-927 (1997).
Dinter et al., Biotechnol. Lett., vol. 22(1), pp. 25-30 (2000).
Dube et al., J. Biol. Chem., vol. 263(33), pp. 17516-17521 (1988).
Dudziak et al., Tetrahedron, 2000, vol. 56(32), pp. 5865-5869.
Dumas et al., Bioorg. Med. Chem. Lett., vol. 1(8), pp. 425-428 (1991).
Ernst et al., 1999, Glycoconj. J. 16(2):161-170.
Fairhall et al., Endocrinology, vol. 131(4), pp. 1963-1969 (1992).
Feldman et al., Proc. Natl. Acad. Sci. USA, vol. 102(8), pp. 3016-3021 (2005).
Gross et al., Analytic Biochemistry, 1990, vol. 186, pp. 127-134.
Hansen et al., Biochem. J., vol. 308, pp. 801-813 (1995).
Haro et al., Biochem. Biophys. Res.Comm., vol. 228(2), pp. 549-556 (1996).
Jezek et al., J. Peptide Sci., vol. 5, pp. 46-55 (1999).
Kaneko et al., Febs Lett., vol. 452(3), pp. 237-242 (1999).
Keene et al., J. Biol. Chem., vol. 264(9), pp. 4769-4775 (1989).
Kimura et al., Proc. Natl. Acad.Sci. USA, vol. 96(8), pp. 4530-4535 (1999).
Kisselev, Structure, vol. 10(1), pp. 8-9 (2002).
Kukowska-Latallo et al., Genes Dev., vol. 4(8), pp. 1288-1303 (1990).
Leist et al., Science, vol. 305, pp. 239-242 (2004).
Leiter et al., J. Biol. Chem., vol. 274(31), pp. 21830-2189 (1999).
Luo et al., Nature, 1997, vol. 386, pp. 78-81.
Makino, Y. et al., Journal of Biological Chemistry, 2000, vol. 128, pp. 175-180.
Malissard et al., Biochem. Biophys. Res.Commun., vol. 267(1), pp. 169-173 (2000).
Manfioletti et al., Molecular and Cellular Biology, 1993, vol. 13(8), pp. 4976-4985.
Mollicone et al., Eur. J. Biochem., vol. 191(1), pp. 169-176 (1990).
Monaco et al., Gene, vol. 180, pp. 145-150 (1996).
Nelsestuen, G. et al., Vitamins and Hormones, 2000, vol. 58, pp. 355-389.
Ngo et al., 1994, "Computational Complexity, Protein Structure Prediction, and the Levinthal Paradox," The Protein Folding Problem and Tertiary Structure Prediction, Chapter 14, pp. 433-440.
Oh-Eda et al., J. Biol. Chem., vol. 265, pp. 11432-11435 (1990).
Palcic et al., Carbohydr. Res., vol. 190(1), pp. 1-11 (1989).
Patra et al., 2000, Protein Expression and Purification, vol. 18, pp. 182-190.
Prati et al., Biotech and Bioeng., vol. 79(5), pp. 580-585 (2002).
Prieels et al., J. Biol. Ciiem., vol. 256(20), pp. 10456-10463 (1981).
Rasko et al., J. Biol. Chem., vol. 275(7), pp. 4988-49894 (2000).
Seffernick et al., J. Bacteriol., vol. 183(8), pp. 2405-2410 (2001).
Sinclair et al., J. Pharm. Sci., vol. 94, pp. 1626-1635 (2005).
Sørensen, B.B. et al., Journal of Biological Chemistry, 1997, vol. 272(18), pp. 11863-11868.
Tarui et al., 2000, J. Biosci. Bioeng. 90(5):508-514.
Tenno et al., "The Lectin Domain of UDP-Galnac: Polypeptide N-Acetylgalactosaminyltransferase 1 is Involved in O-Glycosylation of a Polypeptide With Multiple Acceptor Sites," 2002, Journal of Biological Chemistry 277(49):47088-47096, (2002).
Trottein et al., Mol. Biochem. Parasitol., vol. 107(2), pp. 279-287 (2000).
Tsuboi et al., Journal of Biological Chemistry, 1996, vol. 271, pp. 27213-2726.
Van Tetering et al., Febs Lett., vol. 461(3), pp. 311-314 (1999).
Veronese, 2001, Biomaterials 22(5):405-417.
Wang et al., Gycobiology, vol. 6(8), pp. 837-842 (1996).
Wang et al., Microbiol., vol. 145(Pt. 11), pp. 3245-3253 (1999).
Wishart et al., J. Biol. Chem., vol. 270(45), pp. 26782-26785 (1995).
Witkowski et al., Biochemistry, vol. 38(36), pp. 11643-11650 (1999).
Non-Final Office Action Mailed Jan. 6, 2010 in U.S. Appl. No. 11/656,643 Filed Jan. 23, 2007; First Named Inventor: Defrees.
Non-Final Office Action Mailed Sep. 22, 2010 in U.S. Appl. No. 11/982,273 Filed Nov. 24, 2004; First Named Inventor: Defrees.
Non-Final Office Action Mailed Jan. 10, 2011 in U.S. Appl. No. 11/659,942 Filed Sep. 12, 2005; First Named Inventor: Defrees.
Non-Final Office Action Mailed May 26, 2010 in U.S. Appl. No. 11/866,969 Filed Oct. 3, 2007; First Named Inventor: Defrees.

Final Office Action Mailed Nov. 24, 2010 in U.S. Appl. No. 11/866,969 Filed Oct. 3, 2007; First Named Inventor: Defrees.
Non-Final Office Action Mailed Jun. 16, 2010 in U.S. Appl. No. 11/843,588 Filed Aug. 22, 2007; First Named Inventor: Defrees.
Final Office Action Mailed Jan. 21, 2011 in U.S. Appl. No. 11/843,588 Filed Aug. 22, 2007; First Named Inventor: Defrees.
Non-Final Office Action Mailed Mar. 31, 2008 in U.S. Appl. No. 10/549,528 Filed Sep. 19, 2005; First Named Inventor: Defrees.
Final Office Action Mailed Jan. 6, 2009 in U.S. Appl. No. 10/549,528 Filed Sep. 19, 2005; First Named Inventor: Defrees.
Notice of Allowance Mailed Nov. 9, 2009 in U.S. Appl. No. 10/549,528 Filed Sep. 19, 2005; First Named Inventor: Defrees.
Non-Final Office Action Mailed Aug. 5, 2010 in U.S. Appl. No. 12/496,595 Filed Jul. 1, 2009; First Named Inventor: Defrees.
English Abstract of JP 59-172425 Filed Sep. 29, 1984.
Abstract of WO9215686 Which Corresponds to JP6-504678 Filed Jun. 2, 1994.
Abstract of WO9502683 Which Corresponds to JP-9503905 Filed Apr. 22, 1997.
Guo et al., Applied Biochemistry an Biotechnology, 1997, vol. 68, No. 1/02, pp. 1-20.
Gross et al., European Journal of Biochemistry, 1988, vol. 177, No. 3, pp. 583-589.

* cited by examiner

FIG: 1 amino acid sequence of wild-type human Factor VII:

```
Ala-Asn-Ala-Phe-Leu-GLA-GLA-Leu-Arg-Pro-Gly-Ser-Leu-GLA-Arg-GLA-Cys-Lys-
                5                   10                  15

GLA-GLA-Gln-Cys-Ser-Phe-GLA-GLA-Ala-Arg-GLA-Ile-Phe-Lys-Asp-Ala-GLA-Arg-
      20                  25                  30                  35

Thr-Lys-Leu-Phe-Trp-Ile-Ser-Tyr-Ser-Asp-Gly-Asp-Gln-Cys-Ala-Ser-Ser-Pro-
            40                  45                  50

Cys-Gln-Asn-Gly-Gly-Ser-Cys-Lys-Asp-Gln-Leu-Gln-Ser-Tyr-Ile-Cys-Phe-Cys-
 55                  60                  65                  70

Leu-Pro-Ala-Phe-Glu-Gly-Arg-Asn-Cys-Glu-Thr-His-Lys-Asp-Asp-Gln-Leu-Ile-
            75                  80                  85                  90

Cys-Val-Asn-Glu-Asn-Gly-Gly-Cys-Glu-Gln-Tyr-Cys-Ser-Asp-His-Thr-Gly-Thr-
                95                  100                 105

Lys-Arg-Ser-Cys-Arg-Cys-His-Glu-Gly-Tyr-Ser-Leu-Leu-Ala-Asp-Gly-Val-Ser-
      110                 115                 120                 125

Cys-Thr-Pro-Thr-Val-Glu-Tyr-Pro-Cys-Gly-Lys-Ile-Pro-Ile-Leu-Glu-Lys-Arg-
            130                 135                 140

Asn-Ala-Ser-Lys-Pro-Gln-Gly-Arg-Ile-Val-Gly-Gly-Lys-Val-Cys-Pro-Lys-Gly-
145                 150                 155                 160

Glu-Cys-Pro-Trp-Gln-Val-Leu-Leu-Leu-Val-Asn-Gly-Ala-Gln-Leu-Cys-Gly-Gly-
            165                 170                 175                 180

Thr-Leu-Ile-Asn-Thr-Ile-Trp-Val-Val-Ser-Ala-Ala-His-Cys-Phe-Asp-Lys-Ile-
                185                 190                 195
```

FIG: 1 (continued)

```
Lys-Asn-Trp-Arg-Asn-Leu-Ile-Ala-Val-Leu-Gly-Glu-His-Asp-Leu-Ser-Glu-His-
        200                 205                 210                 215

Asp-Gly-Asp-Glu-Gln-Ser-Arg-Arg-Val-Ala-Gln-Val-Ile-Ile-Pro-Ser-Thr-Tyr-
            220                 225                 230
Val-Pro-Gly-Thr-Thr-Asn-His-Asp-Ile-Ala-Leu-Leu-Arg-Leu-His-Gln-Pro-Val-
235                 240                 245                 250

Val-Leu-Thr-Asp-His-Val-Val-Pro-Leu-Cys-Leu-Pro-Glu-Arg-Thr-Phe-Ser-Glu-
        255                 260                 265                 270

Arg-Thr-Leu-Ala-Phe-Val-Arg-Phe-Ser-Leu-Val-Ser-Gly-Trp-Gly-Gln-Leu-Leu-
            275                 280                 285

Asp-Arg-Gly-Ala-Thr-Ala-Leu-Glu-Leu-Met-Val-Leu-Asn-Val-Pro-Arg-Leu-Met-
        290                 295                 300             305 306

Thr-Gln-Asp-Cys-Leu-Gln-Gln-Ser-Arg-Lys-Val-Gly-Asp-Ser-Pro-Asn-Ile-Thr-
            310                 315                 320

Glu-Tyr-Met-Phe-Cys-Ala-Gly-Tyr-Ser-Asp-Gly-Ser-Lys-Asp-Ser-Cys-Lys-Gly-
325                 330                 335                 340

Asp-Ser-Gly-Gly-Pro-His-Ala-Thr-His-Tyr-Arg-Gly-Thr-Trp-Tyr-Leu-Thr-Gly-
        345                 350                 355                 360

Ile-Val-Ser-Trp-Gly-Gln-Gly-Cys-Ala-Thr-Val-Gly-His-Phe-Gly-Val-Tyr-Thr-
            365                 370                 375

Arg-Val-Ser-Gln-Tyr-Ile-Glu-Trp-Leu-Gln-Lys-Leu-Met-Arg-Ser-Glu-Pro-Arg-
        380                 385                 390                 395

Pro-Gly-Val-Leu-Leu-Arg-Ala-Pro-Phe-Pro
            400                 405
```

PEGYLATED FACTOR VII GLYCOFORMS

CROSS-REFERENCE TO RELATED APPLICATIONS

This application is a continuation of U.S. patent application Ser. No. 11/845,175, filed Aug. 27, 2007, now abandoned, which is a continuation of U.S. patent application Ser. No. 10/609,701, filed Jun. 30, 2003, now abandoned, which is a continuation of International Application No. PCT/DK03/00420, filed Jun. 20, 2003, and claims priority under 35 U.S.C. 119 of Danish Application No. PA 2002 00964, filed Jun. 21, 2002, and U.S. Application No. 60/394,778, filed Jul. 2, 2002, the contents of which are fully incorporated herein by reference.

FIELD OF THE INVENTION

The present invention relates to compositions comprising Factor VII conjugates having predetermined patterns of glycosylation.

BRIEF DESCRIPTION OF THE DRAWINGS

FIG. 1 sets forth the amino acid sequence of wild-type human Factor VII.

BACKGROUND OF THE INVENTION

Factor VII is a vitamin K-dependent plasma protein synthesized in the liver and secreted into the blood as a single chain glycoprotein with a molecular weight of approximately 50 kDa. The FVII zymogen is converted into an activated form (FVIIa) by proteolytic cleavage. FVIIa in complex with tissue factor (TF) is able to convert both Factor IX and Factor X into their activated forms, followed by reactions leading to rapid thrombin generation and fibrin formation.

The proteins involved in the clotting cascade, including, e.g., Factor VII, Factor VIII, Factor IX, Factor X, and Protein C, are proving to be useful therapeutic agents to treat a variety of pathological conditions. Accordingly, there is an increasing need for formulations comprising these proteins that are pharmaceutically acceptable and exhibit a uniform and predetermined clinical efficacy.

Because of the many disadvantages of using human plasma as a source of pharmaceutical products, it is preferred to produce these proteins in recombinant systems. The clotting proteins, however, are subject to a variety of co- and post-translational modifications, including, e.g., asparagine-linked (N-linked) glycosylation; O-linked glycosylation; and γ-carboxylation of glu residues. These modifications may be qualitatively or quantitatively different when heterologous cells are used as hosts for large-scale production of the proteins. In particular, production in heterologous cells often results in a different array of glycoforms, which are identical polypeptides having different covalently linked oligosaccharide structures.

In different systems, variations in the oligosaccharide structure of therapeutic proteins have been linked to, inter alia, changes in immunogenicity and in vivo clearance.

Besides in vivo clearance also functional in vivo half-life is of importance to the period of time during which the compound is "therapeutically available" in the body.

The circulating half-life of rFVIIa is about 2.3 hours ("Summary Basis for Approval for NovoSeven©", FDA reference number 96-0597).

Commercial preparations of human recombinant FVIIa are sold as NovoSeven®. NovoSeven® is the only rFVIIa for effective and reliable treatment of bleeding episodes available on the market. Relatively high doses and frequent administration are necessary to reach and sustain the desired therapeutic or prophylactic effect. As a consequence adequate dose regulation is difficult to obtain and the need of frequent intravenous administrations imposes restrictions on the patient's way of living.

A molecule with a longer circulation half-life would decrease the number of necessary administrations. Given the association of current FVIIa product with frequent injections, there is a clear need for improved FVII molecules.

One way of improving the circulation is to ensure that the rate of clearance from the body is reduced. As said, variations in the oligosaccharide structure of therapeutic proteins have been linked to, inter alia, in vivo clearance. Furthermore, attachment of a chemical moiety to the polypeptide may confer reduced renal clearance to the polypeptide.

Inactive forms of FVII have been reported. The inactivated form is capable of competing with wild type FVII or FVIIa for binding to tissue factor and inhibiting clotting activity. The inactivated form of FVIIa is suggested to be used for treatment of patients being in hypercoagulable states, such as patients with sepsis, in risk of myocardial infarction or of thrombotic stroke.

WO 98/32466 suggests that FVII, among many other proteins, may be PEGylated but does not contain any further information in this respect.

WO 01/58935 claims conjugates of non-polypeptide moieties (e.g., PEG) with a polypeptide wherein the amino acid sequence differs from that of wild-type FVII in that at least one amino acid residue comprising an attachment group for a non-peptidic moiety has been introduced or removed.

U.S. Pat. No. 4,847,325 suggests that colony stimulating factor-1 (CSF-1) could be attached to PEG by reacting PEG derivatives with oxidized CSF-1.

Thus, there is a need in the art for compositions and methods that provide clotting protein preparations, particularly preparations comprising improved recombinant human Factor VII, modified Factor VII, or Factor VII-related polypeptide.

SUMMARY OF THE INVENTION

It has been found by the present investigators that preparations of Factor VII polypeptides having glycoform patterns which contain at least one oligosaccharide group covalently linked to at least one polymeric group exhibit improved functional properties. Accordingly, the present invention relates to methods and compositions that provide these conjugate protein preparations.

Accordingly, the present invention relates in a first aspect to a preparation comprising a plurality of Factor VII polypeptides or Factor VII-related polypeptides, wherein the polypeptides comprise asparagine-linked and/or serine-linked oligosaccharide chains, and wherein at least one oligosaccharide group is covalently attached to at least one polymeric group.

In one embodiment thereof, the polymeric group is covalently attached to a sialic acid moiety. In another embodiment thereof, the polymeric group is covalently attached to a galactose moiety.

In one embodiment thereof, between about 94-100% of the oligosaccharide chains comprise at least one sialic acid moiety.

In one embodiment thereof, between about 94-100% of the oligosaccharide chains comprise at least one sialic acid moiety, and wherein less than about 25% of the oligosaccharide chains contains at least one uncapped antenna.

In one embodiment, less than about 10% of the oligosaccharide chains contains at least one uncapped antenna In one embodiment, less than about 5, preferably less than about 2% of the oligosaccharide chains contain at least one uncapped antenna.

In one embodiment, between about 96-100% of the oligosaccharide chains comprise at least one sialic acid moiety.

In one embodiment, between about 98-100% of the oligosaccharide chains comprise at least one sialic acid moiety.

In one embodiment, the asparagine-linked oligosaccharide chains are located in positions corresponding to amino acid residues Asn-145 and Asn-322 of wild-type human FVIIa (FIG. 1).

In one embodiment, the serine-linked oligosaccharide chains are located in positions corresponding to amino acid residues Ser-52 and Ser-60 of wild-type human FVIIa (FIG. 1).

In one embodiment, the polymers are selected from the group of: polyalkylene oxide (PAO), including polyalkylene glycol (PAG), such as polyethylene glycol (PEG) and polypropylene glycol (PPG), branched PEGs, polyvinyl alcohol (PVA), polycarboxylate, poly-vinylpyrolidone, polyethylene-co-maleic acid anhydride, polystyrene-co-maleic acid anhydride, and dextran, including carboxymethyl-dextran, polyurethaner, polyestre and polyamider.

In one embodiment, the polymer is a polyethylene glycol (PEG); In one embodiment, the polyethylene glycol is PEG with a molecular weight of 300-100,000 Da, such as about 500-20,000 Da., or about 500-15,000 Da, or 2-15 kDa, or 3-15 kDa, or 3-12 kDa, or about 10 kDa.

In one embodiment, the polypeptide has the amino acid sequence of wild-type Factor VII (FIG. 1). In one embodiment, the polypeptides are wild-type Factor VIIa.

In one embodiment, the Factor VII polypeptides are selected from the group consisting of: S52A-Factor VII, S60A-Factor VII, Factor VII that has been proteolytically cleaved between residues 290 and 291; Factor VII that has been proteolytically cleaved between residues 315 and 316; Factor VII that has been oxidized, L305V-FVII, L305V/M306D/D309S-FVII, L305I-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, S336G-FVII; Factor VII-sequence variants wherein the amino acid residue in positions 290 and/or 291, preferably 290, have been replaced; and Factor VII-sequence variants wherein the amino acid residue in positions 315 and/or 316, preferably 315, have been replaced. In another embodiment the Factor VII polypeptides are selected from the list consisting of: Factor VII variants having increased biological activity compared to wild-type FVIIa as disclosed in WO 01/83725, WO 02/22776, WO 02/77218, WO 03/27147, and WO 03/37932; L305V/K337A-FVII, L305V/V158D-FVII, L305V/E296V-FVII, L305V/M298Q-FVII, L305V/V158T-FVII, L305V/K337A/V158T-FVII, L305V/K337A/M298Q-FVII, L305V/K337A/E296V-FVII, L305V/K337A/V158D-FVII, L305V/V158D/M298Q-FVII, L305V/V158D/E296V-FVII, L305V/V158T/M298Q-FVII, L305V/V158T/E296V-FVII, L305V/E296V/M298Q-FVII, L305V/V158D/E296V/M298Q-FVII, L305V/V158T/E296V/M298Q-FVII, L305V/V158T/K337A/M298Q-FVII, L305V/V158T/E296V/K337A-FVII, L305V/V158D/K337A/M298Q-FVII, L305V/V158D/E296V/K337A-FVII, L305V/V158D/E296V/M298Q/K337A-FVII, L305V/V158T/E296V/M298Q/K337A-FVII, S314E/K316H-FVII, S314E/K316Q-FVII, S314E/L305V-FVII, S314E/K337A-FVII, S314E/V158D-FVII, S314E/E296V-FVII, S314E/M298Q-FVII, S314E/V158T-FVII, K316H/L305V-FVII, K316H/K337A-FVII, K316H/V158D-FVII, K316H/E296V-FVII, K316H/M298Q-FVII, K316H/V158T-FVII, K316Q/L305V-FVII, K316Q/K337A-FVII, K316Q/V158D-FVII, K316Q/E296V-FVII, K316Q/M298Q-FVII, K316Q/V158T-FVII, S314E/L305V/K337A-FVII, S314E/L305V/V158D-FVII, S314E/L305V/E296V-FVII, S314E/L305V/M298Q-FVII, S314E/L305V/V158T-FVII, S314E/L305V/K337A/V158T-FVII, S314E/L305V/K337A/M298Q-FVII, S314E/L305V/K337A/E296V-FVII, S314E/L305V/K337A/V158D-FVII, S314E/L305V/V158D/M298Q-FVII, S314E/L305V/V158D/E296V-FVII, S314E/L305V/V158T/M298Q-FVII, S314E/L305V/V158T/E296V-FVII, S314E/L305V/E296V/M298Q-FVII, S314E/L305V/V158D/E296V/M298Q-FVII, S314E/L305V/V158T/E296V/M298Q-FVII, S314E/L305V/V158T/K337A/M298Q-FVII, S314E/L305V/V158T/E296V/K337A-FVII, S314E/L305V/V158D/K337A/M298Q-FVII, S314E/L305V/V158D/E296V/K337A-FVII, S314E/L305V/V158D/E296V/M298Q/K337A-FVII, S314E/L305V/V158T/E296V/M298Q/K337A-FVII, K316H/L305V/K337A-FVII, K316H/L305V/V158D-FVII, K316H/L305V/E296V-FVII, K316H/L305V/M298Q-FVII, K316H/L305V/V158T-FVII, K316H/L305V/K337A/V158T-FVII, K316H/L305V/K337A/M298Q-FVII, K316H/L305V/K337A/E296V-FVII, K316H/L305V/K337A/V158D-FVII, K316H/L305V/V158D/M298Q-FVII, K316H/L305V/V158D/E296V-FVII, K316H/L305V/V158T/M298Q-FVII, K316H/L305V/V158T/E296V-FVII, K316H/L305V/E296V/M298Q-FVII, K316H/L305V/V158D/E296V/M298Q-FVII, K316H/L305V/V158T/E296V/M298Q-FVII, K316H/L305V/V158T/K337A/M298Q-FVII, K316H/L305V/V158T/E296V/K337A-FVII, K316H/L305V/V158D/K337A/M298Q-FVII, K316H/L305V/V158D/E296V/K337A-FVII, K316H/L305V/V158D/E296V/M298Q/K337A-FVII, K316H/L305V/V158T/E296V/M298Q/K337A-FVII, K316Q/L305V/K337A-FVII, K316Q/L305V/V158D-FVII, K316Q/L305V/E296V-FVII, K316Q/L305V/M298Q-FVII, K316Q/L305V/V158T-FVII, K316Q/L305V/K337A/V158T-FVII, K316Q/L305V/K337A/M298Q-FVII, K316Q/L305V/K337A/E296V-FVII, K316Q/L305V/K337A/V158D-FVII, K316Q/L305V/V158D/M298Q-FVII, K316Q/L305V/V158D/E296V-FVII, K316Q/L305V/V158T/M298Q-FVII, K316Q/L305V/V158T/E296V-FVII, K316Q/L305V/E296V/M298Q-FVII, K316Q/L305V/V158D/E296V/M298Q-FVII, K316Q/L305V/V158T/E296V/M298Q-FVII, K316Q/L305V/V158T/K337A/M298Q-FVII, K316Q/L305V/V158T/E296V/K337A-FVII, K316Q/L305V/V158D/K337A/M298Q-FVII, K316Q/L305V/V158D/E296V/K337A-FVII, K316Q/L305V/V158D/E296V/M298Q/K337A-FVII, K316Q/L305V/V158T/E296V/M298Q/K337A-FVII, F374Y/K337A-FVII, F374Y/V158D-FVII, F374Y/E296V-FVII, F374Y/M298Q-FVII, F374Y/V158T-FVII, F374Y/S314E-FVII, F374Y/L305V-FVII, F374Y/L305V/K337A-FVII, F374Y/L305V/V158D-FVII, F374Y/L305V/E296V-FVII, F374Y/L305V/M298Q-FVII, F374Y/L305V/V158T-FVII, F374Y/L305V/S314E-FVII, F374Y/K337A/S314E-FVII, F374Y/K337A/V158T-FVII, F374Y/K337A/M298Q-FVII, F374Y/K337A/E296V-FVII, F374Y/K337A/V158D-FVII, F374Y/V158D/S314E-FVII, F374Y/

V158D/M298Q-FVII, F374Y/V158D/E296V-FVII, F374Y/ V158T/S314E-FVII, F374Y/V158T/M298Q-FVII, F374Y/ V158T/E296V-FVII, F374Y/E296V/S314E-FVII, F374Y/ S314E/M298Q-FVII, F374Y/E296V/M298Q-FVII, F374Y/ L305V/K337A/V158D-FVII, F374Y/L305V/K337A/ E296V-FVII, F374Y/L305V/K337A/M298Q-FVII, F374Y/ L305V/K337A/V158T-FVII, F374Y/L305V/K337A/ S314E-FVII, F374Y/L305V/V158D/E296V-FVII, F374Y/ L305V/V158D/M298Q-FVII, F374Y/L305V/V158D/ S314E-FVII, F374Y/L305V/E296V/M298Q-FVII, F374Y/ L305V/E296V/V158T-FVII, F374Y/L305V/E296V/S314E-FVII, F374Y/L305V/M298Q/V158T-FVII, F374Y/L305V/ M298Q/S314E-FVII, F374Y/L305V/V158T/S314E-FVII, F374Y/K337A/S314E/V158T-FVII, F374Y/K337A/S314E/ M298Q-FVII, F374Y/K337A/S314E/E296V-FVII, F374Y/ K337A/S314E/V158D-FVII, F374Y/K337A/V158T/ M298Q-FVII, F374Y/K337A/V158T/E296V-FVII, F374Y/ K337A/M298Q/E296V-FVII, F374Y/K337A/M298Q/ V158D-FVII, F374Y/K337A/E296V/V158D-FVII, F374Y/ V158D/S314E/M298Q-FVII, F374Y/V158D/S314E/ E296V-FVII, F374Y/V158D/M298Q/E296V-FVII, F374Y/ V158T/S314E/E296V-FVII, F374Y/V158T/S314E/ M298Q-FVII, F374Y/V158T/M298Q/E296V-FVII, F374Y/ E296V/S314E/M298Q-FVII, F374Y/L305V/M298Q/ K337A/S314E-FVII, F374Y/L305V/E296V/K337A/ S314E-FVII, F374Y/E296V/M298Q/K337A/S314E-FVII, F374Y/L305V/E296V/M298Q/K337A-FVII, F374Y/ L305V/E296V/M298Q/S314E-FVII, F374Y/V158D/ E296V/M298Q/K337A-FVII, F374Y/V158D/E296V/ M298Q/S314E-FVII, F374Y/L305V/V158D/K337A/ S314E-FVII, F374Y/V158D/M298Q/K337A/S314E-FVII, F374Y/V158D/E296V/K337A/S314E-FVII, F374Y/ L305V/V158D/E296V/M298Q-FVII, F374Y/L305V/ V158D/M298Q/K337A-FVII, F374Y/L305V/V158D/ E296V/K337A-FVII, F374Y/L305V/V158D/M298Q/ S314E-FVII, F374Y/L305V/V158D/E296V/S314E-FVII, F374Y/V158T/E296V/M298Q/K337A-FVII, F374Y/ V158T/E296V/M298Q/S314E-FVII, F374Y/L305V/ V158T/K337A/S314E-FVII, F374Y/V158T/M298Q/ K337A/S314E-FVII, F374Y/V158T/E296V/K337A/ S314E-FVII, F374Y/L305V/V158T/E296V/M298Q-FVII, F374Y/L305V/V158T/M298Q/K337A-FVII, F374Y/ L305V/V158T/E296V/K337A-FVII, F374Y/L305V/ V158T/M298Q/S314E-FVII, F374Y/L305V/V158T/ E296V/S314E-FVII, F374Y/E296V/M298Q/K337A/ V158T/S314E-FVII, F374Y/V158D/E296V/M298Q/ K337A/S314E-FVII, F374Y/L305V/V158D/E296V/ M298Q/S314E-FVII, F374Y/L305V/E296V/M298Q/ V158T/S314E-FVII, F374Y/L305V/E296V/M298Q/ K337A/V158T-FVII, F374Y/L305V/E296V/K337A/ V158T/S314E-FVII, F374Y/L305V/M298Q/K337A/ V158T/S314E-FVII, F374Y/L305V/V158D/E296V/ M298Q/K337A-FVII, F374Y/L305V/V158D/E296V/ K337A/S314E-FVII, F374Y/L305V/E296V/M298Q/ K337A/V158T/S314E-FVII, F374Y/L305V/V158D/ E296V/M298Q/K337A/S314E-FVII, S52A-Factor VII, S60A-Factor VII; and P11Q/K33E-FVII, T106N-FVII, K143N/N145T-FVII, V253N-FVII, R290N/A292T-FVII, G291N-FVII, R315N/V317T-FVII, K143N/N145T/R315N/ V317T-FVII; FVII having substitutions, additions or deletions in the amino acid sequence from 233Thr to 240Asn, FVII having substitutions, additions or deletions in the amino acid sequence from 304Arg to 329Cys, and FVII having substitutions, deletions, additions in the amino acid sequence Ile153-Arg223.

In one embodiment, the Factor VII-related polypeptides are selected from the group consisting of: R152E-Factor VII, S344A-Factor VII, FFR-Factor VII, and Factor VIIa lacking the Gla domain.

In one embodiment, the Factor VII-related polypeptide exhibit at least about 25%, preferably at least about 50%, more preferably at least about 75% and most preferably at least about 90% of the specific activity of wild-type Factor VIIa that has been produced in the same cell type, when tested in one or more of a clotting assay, proteolysis assay, or TF binding assay as described in the present specification.

In one embodiment, the Factor VII-related polypeptide exhibit less than about 25%, preferably less than about 10%, more preferably less than about 5% and most preferably less than about 1% of the specific activity of wild-type Factor VIIa that has been produced in the same cell type when tested in one or more of a clotting assay, proteolysis assay, or TF binding assay as described in the present specification.

In different embodiments, the conjugated polypeptide exhibits a bioavailability that is at least about 110% of the bioavailability of a reference preparation, such as at least about 120%, or at least about 130%, or at least about 140% of the bioavailability of the reference preparation.

In one embodiment, the conjugated polypeptide exhibits a serum half-life that is at least about 125% of the half-life of a reference preparation, such as at least about 150%, or at least about 200%, or at least about 250% of the half-life of the reference preparation.

In one embodiment, the conjugated polypeptide is made by enzymatic modification of sialic or galactose moieties in the polypeptide.

In a further aspect, the invention relates to a method of preparing the preparation of Factor VII polypeptides as described herein, the method comprising the step of contacting the oligosaccharide-containing polypeptide with a polymer molecule under conditions in which the at least one polymer molecule is covalently attached to at least one of the oligosaccharide chains of the polypeptides.

In a still further aspect, the invention relates to a pharmaceutical composition comprising a preparation of Factor VII polypeptides as described herein and a pharmaceutically acceptable carrier or adjuvant.

In a still further aspect, the invention relates to the use of a preparation comprising a plurality of Factor VII polypeptides or Factor VII-related polypeptides, wherein the polypeptides comprise asparagine-linked and/or serine-linked oligosaccharide chains, and wherein at least one oligosaccharide group is covalently attached to at least one polymeric group, for the manufacture of a medicament for treating a Factor VII-responsive syndrome.

In a still further aspect, the invention relates to a method for treating a Factor VII-responsive syndrome, the method comprising administering a pharmaceutical formulation comprising the preparation of Factor VII polypeptides as described herein to a patient in need of such treatment, under conditions that result in a decrease in bleeding and/or an increase in blood clotting.

In one embodiment thereof, the syndrome is selected from the group consisting of haemophilia A, haemophilia B, Factor XI deficiency, Factor VII deficiency, thrombocytopenia, von Willebrand's disease, presence of a clotting factor inhibitor, surgery, trauma, anticoagulant therapy, including dilutional coagulopathy, intercranial haemorrhage, stem cell transplantation, upper gastrointestinal bleedings, and liver disease.

In a still further aspect, the invention relates to a method for preventing unwanted bleeding, the method comprising administering a pharmaceutical formulation comprising the preparation of Factor VII polypeptides as described herein to a patient in need of such treatment, under conditions that result in a decrease in bleeding and/or an increase in blood clotting.

In a still further aspect, the invention relates to a method for preventing unwanted blood clotting, the method comprising administering a pharmaceutical formulation comprising the preparation of Factor VII polypeptides as described herein to a patient in need of such treatment, under conditions effective for inhibiting coagulation.

In one embodiment thereof, the unwanted blood clotting is associated with a condition selected from the group consisting of: angioplasty, deep vein thrombosis, pulmonary embolism, stroke, disseminated intravascular coagulation (DIC), fibrin deposition in lungs and kidneys associated with gram-negative endotoxemia, and myocardial infarction In a still further aspect, the invention relates to a method for preventing tissue factor mediated reactions, the method comprising administering a pharmaceutical formulation comprising the preparation of Factor VII polypeptides as described herein to a patient in need of such treatment, under conditions effective for inhibiting coagulation.

In one embodiment thereof, the tissue factor mediated reactions are associated with a condition selected from the group consisting of inflammation, cancer, tumour growth, metastasis, angiogenesis, SIRS, ALI, ARDS, MOF, HUS, and TTP

DESCRIPTION OF THE INVENTION

The present inventors have discovered that preparations of coagulation proteins having glycoform patterns wherein at least one oligosaccharide group is covalently linked to at least one polymeric group, such as, e.g., PEG, exhibit improved functional properties. Accordingly, the present invention relates to methods and compositions that provide these conjugate protein preparations. In particular, the invention relates to preparations comprising Factor VII polypeptides and Factor VII-related polypeptides having patterns of asparagine-linked (N-linked) and serine-linked (O-linked) oligosaccharides covalently attached to at least one polymeric group. The preparations of the invention exhibit altered properties, including, without limitation, improved pharmacokinetic properties, and improved clinical efficacy. The invention also encompasses pharmaceutical formulations that comprise these preparations, as well as therapeutic methods that utilize the formulations.

As used in the present context, the term "covalent attachment" is meant to encompass that the oligosaccharide moiety and the polymeric molecule is either directly covalently joined to one another, or else is indirectly covalently joined to one another through an intervening moiety or moieties, such as a bridge, spacer, or linkage moiety or moieties.

The term "conjugate", or interchangeably "conjugate polypeptide", is intended to indicate a heterogeneous (in the sense of composite or chimeric) molecule formed by the covalent attachment of one or more polypeptides to one or more polymer molecules The term "polymeric molecule", or interchangeably "polymeric group" or "polymeric moiety" or "polymer molecule", encompasses a molecule that is capable of conjugating to an attachment group of the polypeptide. When used in the context of a conjugate of the invention it will be understood that the polymer molecule (or moiety) is linked to the polypeptide part of the conjugate through an attachment group of a oligosaccharide chain of the glycoprotein; preferably, the polymer molecule is attached to a sialic acid moiety capping the oligosaccharide ("sialic acid capping group") or to a galactose moiety.

The polymer molecule is a molecule formed by covalent linkage of two or more monomers wherein none of the monomers is an amino acid residue. Preferred polymers are polymer molecules selected from the group consisting of poly-alkylene oxide (PAO), including polyalkylene glycol (PAG), such as polyethylene glycol (PEG) and polypropylene glycol (PPG), branched PEGs, polyvinyl alcohol (PVA), polycarboxylate, poly-vinylpyrolidone, polyethylene-co-maleic acid anhydride, polystyrene-co-maleic acid anhydride, and dextran, including carboxymethyl-dextran, PEG being particularly preferred.

The term "attachment group" is intended to indicate a functional group of the oligosaccharide moiety capable of attaching a polymer molecule. Useful attachment groups are, for example, amine, hydroxyl, carboxyl, aldehyde, ketone, sulfhydryl, succinimidyl, maleimide, vinylsulfone or haloacetate.

The attachment group on the oligosaccharide moiety may be activated before reaction with the polymer. Alternatively, a group present on the polymer may be activated before reaction with the oligosaccharide moiety. The activated group, whether present on the oligosaccharide- or polymer moiety may be in the form of an activated leaving group.

The term activated leaving group includes those moieties which are easily displaced in organic- or enzyme-regulated substitution reactions. Activated leaving groups are known in the art, see, for example, Vocadlo et al., *In Carbohydrate Chemistry and Biology*, Vol. 2, Wiley-VCH Verlag, Germany (2000); Kodama et al., *Tetrahedron Letters* 34:6419 (1993); Lougheed et al., *J. Biol. Chem.* 274:37717 (1999).

Methods and chemistry for activation of polymers are described in the literature. Commonly used methods for activation of polymers include activation of functional groups with cyanogen bromide, periodate, glutaraldehyde, biepoxides, epichlorohydrin, divinylsulfone, carbodiimide, sulfonyl halides, trichlorotriazine, etc. (see, for example, Taylor (1991), *Protein Immobilization, Fundamentals and Applications*, Marcel Dekker, N.Y.; Wong (1992), *Chemistry of protein Conjugation and Crosslinking*, CRC Press, Boca Raton; Hermanson et al., (1993), *Immobilized Affinity Ligand Techniques*, Academic Press, N.Y.; Dunn et al., Eds. *Polymeric Drugs and Drug Delivery Systems*, ACS Symposium Series Vol. 469, American Chemical Society, 1991.)

Reactive groups and classes of reactions useful in practicing the present invention are generally those which proceed under relatively mild conditions. These include, but are not limited to nucleophilic substitutions (e.g., reaction of amines and alcohols with acyl halides, active esters), electrophilic substitutions (e.g., enamine reactions) and additions to carbon-carbon and carbon-heteroatom bonds (e.g., Michael reaction, Diels-Alder addition). These and other useful reactions are described in, for example, March, *Advanced Organic Chemistry*, $3^{rd}$ edition, John Wiley & Sons, N.Y. 1985; Hermanson, *Bioconjugate Techniques*, Academic Press, San Diego, 1996; Feeney et al, *Modifications of Proteins*, Advances in Chemistry Series, Vol. 198, American Chemical Society, 1982.

The reactive functional groups can be chose such that they do not participate in, or interfere with, the reactions necessary to assemble the oligosaccharide and the polymer moiety. Alternatively, a reactive functional group can be protected from participating in the reaction by the presence of a protective group. For examples of useful protecting groups, see, for example, Greene et al., *Protective groups in Organic Synthesis*, John Wiley & Sons, N.Y., 1991.

General approaches for linking carbohydrates to other molecules are known in the literature (see, e.g., Lee et al., *Biochemistry* 28:1856 (1989); Bhatia et al., *Anal. Biochem.* 178:408 (1989); Janda et al., *J. Am. Chem. Soc.* 112:8886 (1990); and Bednarski et al., WO 92/18135.

The term "naturally occurring glycosylation site" is intended to indicate the glycosylation sites at positions Asn-145 (N145), Asn-322 (N322), Ser-52 (S52), and Ser-60 (S60). In a similar way, the term "naturally occurring in vivo O-glycosylation site" includes the positions S52 and S60, whereas the term "naturally occurring in vivo N-glycosylation site" includes the positions N145 and N322.

The term "functional in vivo half-life" is used in its normal meaning, i.e., the time at which 50% of the biological activity of the polypeptide or conjugate is still present in the body/target organ, or the time at which the activity of the polypeptide or conjugate is 50% of its initial value. As an alternative to determining functional in vivo half-life, "serum half-life" may be determined, i.e., the time at which 50% of the polypeptide or conjugate molecules circulate in the plasma or bloodstream prior to being cleared. Determination of serum-half-life is often more simple than determining functional half-life and the magnitude of serum-half-life is usually a good indication of the magnitude of functional in vivo half-life. Alternative terms to serum half-life include plasma half-life, circulating half-life, circulatory half-life, serum clearance, plasma clearance, and clearance half-life. The polypeptide or conjugate is cleared by the action of one or more of the reticulo-endothelial system (RES), kidney, spleen, or liver, by tissue factor, SEC receptor, or other receptor-mediated elimination, or by specific or unspecific proteolysis. Normally, clearance depends on size (relative to the cut-off for glomerular filtration), charge, attached carbohydrate chains, and the presence of cellular receptors for the protein. The functionality to be retained is normally selected from procoagulant, proteolytic, co-factor binding or receptor binding activity. The functional in vivo half-life and the serum half-life may be determined by any suitable method known in the art as further discussed below (see *Functional Properties of Factor VII Preparations*-section)

The term "increased" as used about the functional in vivo half-life or plasma half-life is used to indicate that the relevant half-life of the polypeptide or conjugate is statistically significantly increased relative to that of a reference molecule, such as non-conjugated Factor VIIa (e.g., wild-type FVIIa) as determined under comparable conditions. For instance the relevant half-life may be increased by at least about 25%, such as by at lest about 50%, e.g., by at least about 100%, 150%, 200%, 250%, or 500%.

"Immunogenicity" of a preparation refers to the ability of the preparation, when administered to a human, to elicit a deleterious immune response, whether humoral, cellular, or both. Factor VIIa polypeptides and Factor VIIa-related polypeptides are not known to elicit detectable immune responses in humans. Nonetheless, in any human sub-population, there may exist individuals who exhibit sensitivity to particular administered proteins. Immunogenicity may be measured by quantifying the presence of anti-Factor VII antibodies and/or Factor VII-responsive T-cells in a sensitive individual, using conventional methods known in the art. In some embodiments, the preparations of the present invention exhibit a decrease in immunogenicity in a sensitive individual of at least about 10%, preferably at least about 25%, more preferably at least about 40% and most preferably at least about 50%, relative to the immunogenicity for that individual of a reference preparation.

The term "amino acid residues corresponding to amino acid residues S52, S60, N145, N322 of FIG. 1 (FVII wt.)" is intended to indicate the Asn and Ser amino acid residues corresponding to the sequence of wild-type Factor VII (FIG. 1) when the sequences are aligned. Amino acid sequence homology/identity is conveniently determined from aligned sequences, using a suitable computer program for sequence alignment, such as, e.g., the ClustalW program, version 1.8, 1999 (Thompson et al., 1994, Nucleic Acid Research, 22: 4673-4680).

Factor VII Polypeptides and Factor VII-Related Polypeptides

The present invention encompasses human Factor VII polypeptides, such as, e.g., those having the amino acid sequence disclosed in U.S. Pat. No. 4,784,950 (wild-type Factor VII). As used herein, "Factor VII" or "Factor VII polypeptide" encompasses wild-type Factor VII, as well as variants of Factor VII exhibiting substantially the same or improved biological activity relative to wild-type Factor VII. The term "Factor VII" is intended to encompass Factor VII polypeptides in their uncleaved (zymogen) form, as well as those that have been proteolytically processed to yield their respective bioactive forms, which may be designated Factor VIIa. Typically, Factor VII is cleaved between residues 152 and 153 to yield Factor VIIa.

As used herein, "Factor VII-related polypeptides" encompasses polypeptides, including variants, in which the Factor VIIa biological activity has been substantially modified or reduced relative to the activity of wild-type Factor VIIa. These polypeptides include, without limitation, Factor VII or Factor VIIa that has been chemically modified and Factor VII variants into which specific amino acid sequence alterations have been introduced that modify or disrupt the bioactivity of the polypeptide.

The biological activity of Factor VIIa in blood clotting derives from its ability to (i) bind to tissue factor (TF) and (ii) catalyze the proteolytic cleavage of Factor IX or Factor X to produce activated Factor IX or X (Factor IXa or Xa, respectively). For purposes of the invention, Factor VIIa biological activity may be quantified by measuring the ability of a preparation to promote blood clotting using Factor VII-deficient plasma and thromboplastin, as described, e.g., in U.S. Pat. No. 5,997,864. In this assay, biological activity is expressed as the reduction in clotting time relative to a control sample and is converted to "Factor VII units" by comparison with a pooled human serum standard containing 1 unit/ml Factor VII activity. Alternatively, Factor VIIa biological activity may be quantified by (i) measuring the ability of Factor VIIa to produce of Factor Xa in a system comprising TF embedded in a lipid membrane and Factor X. (Persson et al., *J. Biol. Chem.* 272:19919-19924, 1997); (ii) measuring Factor X hydrolysis in an aqueous system (see, Example 5 below); (iii) measuring its physical binding to TF using an instrument based on surface plasmon resonance (Persson, *FEBS Letts.* 413:359-363, 1997) (iv) measuring hydrolysis of a synthetic substrate (see, Example 4 below); and (v) measuring generation of thrombin in a TF-independent in vitro system.

Factor VII variants having substantially the same or improved biological activity relative to wild-type Factor VIIa encompass those that exhibit at least about 25%, preferably at least about 50%, more preferably at least about 75% and most preferably at least about 90% of the specific activity of wild-type Factor VIIa that has been produced in the same cell type, when tested in one or more of a clotting assay, proteolysis assay, or TF binding assay as described above. Factor VII variants having substantially reduced biological activity relative to wild-type Factor VIIa are those that exhibit less than about 25%, preferably less than about 10%, more preferably less than about 5% and most preferably less than about 1% of the specific activity of wild-type Factor VIIa that has been produced in the same cell type when tested in one or more of a clotting assay, proteolysis assay, or TF binding assay as described above. Factor VII variants having a substantially modified biological activity relative to wild-type Factor VII include, without limitation, Factor VII variants that exhibit TF-independent Factor X proteolytic activity and those that bind TF but do not cleave Factor X.

Variants of Factor VII, whether exhibiting substantially the same or better bioactivity than wild-type Factor VII, or, alternatively, exhibiting substantially modified or reduced bioactivity relative to wild-type Factor VII, include, without limitation, polypeptides having an amino acid sequence that differs from the sequence of wild-type Factor VII by insertion, deletion, or substitution of one or more amino acids.

Non-limiting examples of Factor VII-related polypeptides having substantially the same or improved biological activity as wild-type Factor VII include S52A-FVII, S60A-FVII (Iino et al., Arch. Biochem. Biophys. 352: 182-192, 1998); L305V-FVII, L305V/M306D/D309S-FVII, L305I-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII; FVIIa variants exhibiting increased proteolytic stability as disclosed in U.S. Pat. No. 5,580,560; Factor VIIa that has been proteolytically cleaved between residues 290 and 291 or between residues 315 and 316 (Mollerup et al., Biotechnol. Bioeng. 48:501-505, 1995); oxidized forms of Factor VIIa (Kornfelt et al., Arch. Biochem. Biophys. 363:43-54, 1999), Factor VII-sequence variants wherein the amino acid residue in positions 290 and/or 291 (of FIG. 1), preferably 290, have been replaced, and Factor VII-sequence variants wherein the amino acid residue in positions 315 and/or 316 (of FIG. 1), preferably 315, have been replaced.

Non-limiting examples of Factor VII-related polypeptides having substantially the same or improved biological activity as wild-type Factor VII further include: FVII variants having increased biological activity compared to wild-type FVIIa as disclosed in WO 01/83725, WO 02/22776, WO 02/77218, WO 03/27147, and WO 03/37932, including, without limitation, L305V-FVII, L305V/M306D/D309S-FVII, L305I-FVII, L305T-FVII, F374P-FVII, V158T/M298Q-FVII, V158D/E296V/M298Q-FVII, K337A-FVII, M298Q-FVII, V158D/M298Q-FVII, L305V/K337A-FVII, V158D/E296V/M298Q/L305V-FVII, V158D/E296V/M298Q/K337A-FVII, V158D/E296V/M298Q/L305V/K337A-FVII, K157A-FVII, E296V-FVII, E296V/M298Q-FVII, V158D/E296V-FVII, V158D/M298K-FVII, and S336G-FVII, L305V/K337A-FVII, L305V/V158D-FVII, L305V/E296V-FVII, L305V/M298Q-FVII, L305V/V158T-FVII, L305V/K337A/V158T-FVII, L305V/K337A/M298Q-FVII, L305V/K337A/E296V-FVII, L305V/K337A/V158D-FVII, L305V/V158D/M298Q-FVII, L305V/V158D/E296V-FVII, L305V/V158T/M298Q-FVII, L305V/V158T/E296V-FVII, L305V/E296V/M298Q-FVII, L305V/V158D/E296V/M298Q-FVII, L305V/V158T/E296V/M298Q-FVII, L305V/V158T/K337A/M298Q-FVII, L305V/V158T/E296V/K337A-FVII, L305V/V158D/K337A/M298Q-FVII, L305V/V158D/E296V/K337A-FVII, L305V/V158D/E296V/M298Q/K337A-FVII, L305V/V158T/E296V/M298Q/K337A-FVII, S314E/K316H-FVII, S314E/K316Q-FVII, S314E/L305V-FVII, S314E/K337A-FVII, S314E/V158D-FVII, S314E/E296V-FVII, S314E/M298Q-FVII, S314E/V158T-FVII, K316H/L305V-FVII, K316H/K337A-FVII, K316H/V158D-FVII, K316H/E296V-FVII, K316H/M298Q-FVII, K316H/V158T-FVII, K316Q/L305V-FVII, K316Q/K337A-FVII, K316Q/V158D-FVII, K316Q/E296V-FVII, K316Q/M298Q-FVII, K316Q/V158T-FVII, S314E/L305V/K337A-FVII, S314E/L305V/V158D-FVII, S314E/L305V/E296V-FVII, S314E/L305V/M298Q-FVII, S314E/L305V/V158T-FVII, S314E/L305V/K337A/V158T-FVII, S314E/L305V/K337A/M298Q-FVII, S314E/L305V/K337A/E296V-FVII, S314E/L305V/K337A/V158D-FVII, S314E/L305V/V158D/M298Q-FVII, S314E/L305V/V158D/E296V-FVII, S314E/L305V/V158T/M298Q-FVII, S314E/L305V/V158T/E296V-FVII, S314E/L305V/E296V/M298Q-FVII, S314E/L305V/V158D/E296V/M298Q-FVII, S314E/L305V/V158T/E296V/M298Q-FVII, S314E/L305V/V158T/K337A/M298Q-FVII, S314E/L305V/V158T/E296V/K337A-FVII, S314E/L305V/V158D/K337A/M298Q-FVII, S314E/L305V/V158D/E296V/K337A-FVII, S314E/L305V/V158D/E296V/M298Q/K337A-FVII, S314E/L305V/V158T/E296V/M298Q/K337A-FVII, K316H/L305V/K337A-FVII, K316H/L305V/V158D-FVII, K316H/L305V/E296V-FVII, K316H/L305V/M298Q-FVII, K316H/L305V/V158T-FVII, K316H/L305V/K337A/V158T-FVII, K316H/L305V/K337A/M298Q-FVII, K316H/L305V/K337A/E296V-FVII, K316H/L305V/K337A/V158D-FVII, K316H/L305V/V158D/M298Q-FVII, K316H/L305V/V158D/E296V-FVII, K316H/L305V/V158T/M298Q-FVII, K316H/L305V/V158T/E296V-FVII, K316H/L305V/E296V/M298Q-FVII, K316H/L305V/V158D/E296V/M298Q-FVII, K316H/L305V/V158T/E296V/M298Q-FVII, K316H/L305V/V158T/K337A/M298Q-FVII, K316H/L305V/V158T/E296V/K337A-FVII, K316H/L305V/V158D/K337A/M298Q-FVII, K316H/L305V/V158D/E296V/K337A-FVII, K316H/L305V/V158D/E296V/M298Q/K337A-FVII, K316H/L305V/V158T/E296V/M298Q/K337A-FVII, K316Q/L305V/K337A-FVII, K316Q/L305V/V158D-FVII, K316Q/L305V/E296V-FVII, K316Q/L305V/M298Q-FVII, K316Q/L305V/V158T-FVII, K316Q/L305V/K337A/V158T-FVII, K316Q/L305V/K337A/M298Q-FVII, K316Q/L305V/K337A/E296V-FVII, K316Q/L305V/K337A/V158D-FVII, K316Q/L305V/V158D/M298Q-FVII, K316Q/L305V/V158D/E296V-FVII, K316Q/L305V/V158T/M298Q-FVII, K316Q/L305V/V158T/E296V-FVII, K316Q/L305V/E296V/M298Q-FVII, K316Q/L305V/V158D/E296V/M298Q-FVII, K316Q/L305V/V158T/E296V/M298Q-FVII, K316Q/L305V/V158T/K337A/M298Q-FVII, K316Q/L305V/V158T/E296V/K337A-FVII, K316Q/L305V/V158D/K337A/M298Q-FVII, K316Q/L305V/V158D/E296V/K337A-FVII, K316Q/L305V/V158D/E296V/M298Q/K337A-FVII, K316Q/L305V/V158T/E296V/M298Q/K337A-FVII, F374Y/K337A-FVII, F374Y/V158D-FVII, F374Y/E296V-FVII, F374Y/M298Q-FVII, F374Y/V158T-FVII, F374Y/S314E-FVII, F374Y/L305V-FVII, F374Y/L305V/K337A-FVII, F374Y/L305V/V158D-FVII, F374Y/L305V/E296V-FVII, F374Y/L305V/M298Q-FVII, F374Y/L305V/V158T-FVII, F374Y/L305V/S314E-FVII, F374Y/K337A/S314E-FVII, F374Y/K337A/V158T-FVII, F374Y/K337A/M298Q-FVII, F374Y/K337A/E296V-FVII, F374Y/K337A/V158D-FVII, F374Y/V158D/S314E-FVII, F374Y/V158D/M298Q-FVII, F374Y/V158D/E296V-FVII, F374Y/V158T/S314E-FVII, F374Y/V158T/M298Q-FVII, F374Y/V158T/E296V-FVII, F374Y/E296V/S314E-FVII, F374Y/

S314E/M298Q-FVII, F374Y/E296V/M298Q-FVII, F374Y/ L305V/K337A/V158D-FVII, F374Y/L305V/K337A/ E296V-FVII, F374Y/L305V/K337A/M298Q-FVII, F374Y/ L305V/K337A/V158T-FVII, F374Y/L305V/K337A/ S314E-FVII, F374Y/L305V/V158D/E296V-FVII, F374Y/ L305V/V158D/M298Q-FVII, F374Y/L305V/V158D/ S314E-FVII, F374Y/L305V/E296V/M298Q-FVII, F374Y/ L305V/E296V/V158T-FVII, F374Y/L305V/E296V/S314E-FVII, F374Y/L305V/M298Q/V158T-FVII, F374Y/L305V/ M298Q/S314E-FVII, F374Y/L305V/V158T/S314E-FVII, F374Y/K337A/S314E/V158T-FVII, F374Y/K337A/S314E/ M298Q-FVII, F374Y/K337A/S314E/E296V-FVII, F374Y/ K337A/S314E/V158D-FVII, F374Y/K337A/V158T/ M298Q-FVII, F374Y/K337A/V158T/E296V-FVII, F374Y/ K337A/M298Q/E296V-FVII, F374Y/K337A/M298Q/ V158D-FVII, F374Y/K337A/E296V/V158D-FVII, F374Y/ V158D/S314E/M298Q-FVII, F374Y/V158D/S314E/ E296V-FVII, F374Y/V158D/M298Q/E296V-FVII, F374Y/ V158T/S314E/E296V-FVII, F374Y/V158T/S314E/ M298Q-FVII, F374Y/V158T/M298Q/E296V-FVII, F374Y/ E296V/S314E/M298Q-FVII, F374Y/L305V/M298Q/ K337A/S314E-FVII, F374Y/L305V/E296V/K337A/ S314E-FVII, F374Y/E296V/M298Q/K337A/S314E-FVII, F374Y/L305V/E296V/M298Q/K337A-FVII, F374Y/ L305V/E296V/M298Q/S314E-FVII, F374Y/V158D/ E296V/M298Q/K337A-FVII, F374Y/V158D/E296V/ M298Q/S314E-FVII, F374Y/L305V/V158D/K337A/ S314E-FVII, F374Y/V158D/M298Q/K337A/S314E-FVII, F374Y/V158D/E296V/K337A/S314E-FVII, F374Y/ L305V/V158D/E296V/M298Q-FVII, F374Y/L305V/ V158D/M298Q/K337A-FVII, F374Y/L305V/V158D/ E296V/K337A-FVII, F374Y/L305V/V158D/M298Q/ S314E-FVII, F374Y/L305V/V158D/E296V/S314E-FVII, F374Y/V158T/E296V/M298Q/K337A-FVII, F374Y/ V158T/E296V/M298Q/S314E-FVII, F374Y/L305V/ V158T/K337A/S314E-FVII, F374Y/V158T/M298Q/ K337A/S314E-FVII, F374Y/V158T/E296V/K337A/ S314E-FVII, F374Y/L305V/V158T/E296V/M298Q-FVII, F374Y/L305V/V158T/M298Q/K337A-FVII, F374Y/ L305V/V158T/E296V/K337A-FVII, F374Y/L305V/ V158T/M298Q/S314E-FVII, F374Y/L305V/V158T/ E296V/S314E-FVII, F374Y/E296V/M298Q/K337A/ V158T/S314E-FVII, F374Y/V158D/E296V/M298Q/ K337A/S314E-FVII, F374Y/L305V/V158D/E296V/ M298Q/S314E-FVII, F374Y/L305V/E296V/M298Q/ V158T/S314E-FVII, F374Y/L305V/E296V/M298Q/ K337A/V158T-FVII, F374Y/L305V/E296V/K337A/ V158T/S314E-FVII, F374Y/L305V/M298Q/K337A/ V158T/S314E-FVII, F374Y/L305V/V158D/E296V/ M298Q/K337A-FVII, F374Y/L305V/V158D/E296V/ K337A/S314E-FVII, F374Y/L305V/V158D/M298Q/ K337A/S314E-FVII, F374Y/L305V/E296V/M298Q/ K337A/V158T/S314E-FVII, F374Y/L305V/V158D/ E296V/M298Q/K337A/S314E-FVII, S52A-Factor VII, S60A-Factor VII; and P11Q/K33E-FVII, T106N-FVII, K143N/N145T-FVII, V253N-FVII, R290N/A292T-FVII, G291N-FVII, R315N/V317T-FVII, K143N/N145T/R315N/ V317T-FVII; FVII having substitutions, additions or deletions in the amino acid sequence from 233Thr to 240Asn, FVII having substitutions, additions or deletions in the amino acid sequence from 304Arg to 329Cys, and FVII having substitutions, deletions, additions in the amino acid sequence Ile153-Arg223.

Non-limiting examples of Factor VII-related polypeptides having substantially reduced or modified biological activity relative to wild-type Factor VII include R152E-FVIIa (Wildgoose et al., *Biochem* 29:3413-3420, 1990), S344A-FVIIa (Kazama et al., *J. Biol. Chem.* 270:66-72, 1995), FFR-FVIIa (Holst et al., *Eur. J. Vasc. Endovasc. Surg.* 15:515-520, 1998), Factor VIIa lacking the Gla domain, (Nicolaisen et al., *FEBS Letts.* 317:245-249, 1993), and Factor VII wherein Lys341 has been replaced by Ala. Non-limiting examples of chemically modified Factor VII polypeptides and sequence variants are described, e.g., in U.S. Pat. No. 5,997,864.

Glycosylation

As used herein, a "pattern" of glycosylation or a glycoform "pattern", "distribution", or "spectrum" refers to the representation of particular oligosaccharide structures within a given population of Factor VII polypeptides or Factor VII-related polypeptides. Non-limiting examples of such patterns include the relative proportion of oligosaccharide chains that (i) have at least one sialic acid residue; (ii) lack any sialic acid residues (i.e., are neutral in charge); (iii) have at least one terminal galactose residue; (iv) have at least one terminal N-acetylgalactosamine residue; (v) have at least one "uncapped" antenna, i.e., have at least one terminal galactose or N-acetylgalactosamine residue; or (vi) have at least one fucose linked $\alpha1\rightarrow3$ to an antennary N-acetylglucosamine residue.

As used herein, an "oligosaccharide chain" refers to the entire oligosaccharide structure that is covalently linked to a single amino acid residue. Factor VII is normally glycosylated at Asn 145 and Asn 322 (N-linked glycosylation) and Ser-52 and Ser-60 (O-linked glycosylation). An N-linked oligosaccharide chain present on Factor VII produced in a human in situ may be bi-, tri, or tetra-antennary, with each antenna having the structure Neu5Ac($\alpha2\rightarrow3$ or $\alpha2\rightarrow6$)Gal ($\beta1\rightarrow4$) GlcNAc linked ($\beta1\rightarrow2$, 4, or 6) to a Man residue which is linked ($\alpha1\rightarrow3$ or 6) to Man($\beta1\rightarrow4$)GlcNAc($\beta1\rightarrow4$) GlcNAc-Asn. (Neu5Ac signifies N-acetylneuraminic acid (sialic acid), Gal signifies galactose, GlcNAc signifies N-acetylglucosamine, and Man signifies mannose). The oligosaccharide chains may also comprise fucose residues, which may be linked $\alpha1\rightarrow6$ to GlcNAc.

An O-linked oligosaccharide chain present on Factor VII produced in a human in situ is mono-antennary with the Ser-52 antenna having the structure Xyl-Xyl-Glc-Ser or Glc-Ser, and the Ser-60 antenna having the structure Neu5Ac ($\alpha2\rightarrow3$ or $\alpha2\rightarrow6$)Gal($\beta1\rightarrow4$)GlcNAc-Fuc-Ser or Fuc-Ser (Fuc signifies fucose, Glc signifies glucose, and Xyl signifies xylose).

When Factor VII is produced in a human in situ, some of the N-linked oligosaccharide chains lack core fucose residues; all of the chains lack antennary fucose residues; and both of the N-linked chains are almost completely sialylated, i.e., the terminal sugar of each antenna is N-acetylneuraminic acid linked to galactose via an $\alpha2\rightarrow3$ or $\alpha2\rightarrow6$ linkage.

When produced in other circumstances, however, Factor VII may contain oligosaccharide chains having different terminal structures on one or more of their antennae, such as, e.g., lacking sialic acid residues; containing N-glycolylneuraminic acid (Neu5Gc) residues; containing a terminal N-acetylgalactosamine (GalNAc) residue in place of galactose; and the like. When produced in, e.g., BHK cells cultured in the presence of calf serum, Factor VII preparations exhibit the following oligosaccharide patterns: 87-93% of the oligosaccharide chains contain at least a single sialic acid residue; 7-13% are neutral (lack any sialic acid); 9-16% contain at least one terminal galactose residue; 19-29% contain at least one terminal N-acetylgalactosamine residue; and 30-39% contain at least one uncapped antenna, i.e., contain at least one terminal galactose or N-acetylgalactosamine residue.

When produced in other types of cells or under other culturing conditions (in a serum-free, fully chemical defined medium), a Factor VII preparation may exhibit the following oligosaccharide patterns (as disclosed in WO 02/29025):

(i) Between about 94-100% of the oligosaccharide chains contain at least one sialic acid residue, such as, e.g., between about 94-99%, between about 95-98%, or between about 96-97%. In different embodiments, at least about 94%, 95%, 96%, or 97% of the oligosaccharide chains contain at least one sialic acid residue.

(ii) 6% or less of the oligosaccharide chains are neutral, such as, e.g., between about 1.5-6% or between about 2-4%.

(iii) Less than about 16%, preferably less than about 10% of the oligosaccharide chains contain at least one terminal galactose, such as, e.g., between about 6-10% or between about 8-9%;

(iv) Less than about 25%, preferably less than about 10% of the oligosaccharide chains contain at least one terminal GalNAc residue, such as, e.g., between about 6-9% or between about 7-8%;

(v) Less than about 30, preferably less than about 25% of the oligosaccharide chains contain at least one uncapped antenna, such as, e.g., between about 11-23% or between about 12-18%; and (vi) At least about 2%, preferably at least about 5%, more preferably at least about 10% or 20%; and most preferably, at least about 40%, of the oligosaccharide chains contain at least one fucose linked α1→3 to an antennary N-acetylglucosamine residue (i.e., an N-acetylglucosamine residue that is linked β1→2, 4, or 6 to a Man residue).

Furthermore, the degree of sialylation (i.e., the number of sialic acid residues attached to each oligosaccharide chain) can be improved by subjecting the expressed Factor VII or Factor VII-related polypeptide-preparation to in vitro enzymatic treatment with a sialyltransferase and an sialic acid donor molecule, e.g., as described in U.S. Pat. No. 6,399,336. In this way, substantially all antennas on the oligosaccharide chains may be sialylated (i.e., "capped" with a sialic acid residue). In some cases, the N-glucans on FVII or FVII related polypeptide is also not fully galactosylated, and a galactosylation step involving galactosyl transferase and UDP-galactose donor substrate prior to the sialylation step will improve the sialic acid content of the product.

The present inventors have produced Factor VII preparations containing oligosaccharide patterns containing at least one polymeric group covalently attached to at least one oligosaccharide group. In one embodiment thereof, the preparations comprise Factor VII polypeptides or Factor VII-related polypeptides exhibiting one or more of the following glycoform patterns:

(i) Between about 94-100% of the oligosaccharide chains contain at least one sialic acid residue, such as, e.g., between about 94-99%, between about 95-98%, or between about 96-97%. In different embodiments, at least about 94%, 95%, 96%, 97%, 98, or 99% of the oligosaccharide chains contain at least one sialic acid residue.

(ii) 6% or less of the oligosaccharide chains are neutral, such as, e.g., between about 0.5-6% or between 1.5-6% or between about 2-4% or between 0.5-4% or between 0.5-2%;

(iii) Less than about 16%, preferably less than about 10% of the oligosaccharide chains contain at least one terminal galactose, such as, e.g., between about 6-10% or between about 8-9%;

(iv) Less than about 25%, preferably less than about 10% of the oligosaccharide chains contain at least one terminal GalNAc residue, such as, e.g., between about 6-9% or between about 7-8%;

(v) Less than about 30, preferably less than about 25% of the oligosaccharide chains contain at least one uncapped antenna, such as, e.g., between about 11-23% or between about 12-18%; and (vi) At least about 2%, preferably at least about 5%, more preferably at least about 10% or 20%; and most preferably, at least about 40%, of the oligosaccharide chains contain at least one fucose linked α1→3 to an antennary N-acetylglucosamine residue (i.e., an N-acetylglucosamine residue that is linked β1→2, 4, or 6 to a Man residue).

It will be understood that each of (i)-(vi) may represent a distinct glycoform pattern that is encompassed by embodiments of the present invention, i.e., the glycoform pattern of a preparation in accordance with the present invention wherein at least one polymeric group is covalently attached to at least one oligosaccharide may be described by only one of (i)-(vi). Alternatively, the glycoform pattern of a preparation encompassed by the invention may be described by more than one of (i)-(vi).

Furthermore, a preparation encompassed by the invention may be described by one or more of (i)-(vi) in combination with one or more other structural features. For example, the invention encompasses preparations comprising Factor VII polypeptides or Factor VII-related polypeptides in which the sialic acid residues (Neu5Ac or Neu5Gc) are linked to galactose exclusively in an α2→3 configuration. The invention also encompasses preparations comprising Factor VII polypeptides or Factor VII-related polypeptides that contain fucose linked α1→6 to a core N-acetylglucosamine and/or fucose linked α1→3 to an antennary N-acetylglucosamine. In one series of embodiments, the preparations of the invention encompass Factor VII or Factor VII-related polypeptides in which more than 99% of the oligosaccharide chains contain at least one sialic acid residue and (a) the sialic acid residues are linked exclusively in an α2→3 configuration and/or (b) there are fucose residues linked to core N-acetylglucosamines and/or (c) a detectable number of antenna terminate in N-acetylgalactosamine. In one embodiment, the invention encompasses preparations comprising wild-type Factor VIIa in which more than 99% of the oligosaccharide chains contain at least one sialic acid residue and the sialic acid residues are linked to galactose exclusively in an α2→3 configuration. In another embodiment, the invention encompasses preparations comprising wild-type Factor VIIa in which more than 99% of the oligosaccharide chains contain at least one sialic acid residue and at least some of the oligosaccharide chains comprise N-acetylgalactosamine.

The pattern of N-linked and/or O-linked oligosaccharides may be determined using any method known in the art, including, without limitation: high-performance liquid chromatography (HPLC); capillary electrophoresis (CE); nuclear magnetic resonance (NMR); mass spectrometry (MS) using ionization techniques such as fast-atom bombardment, electrospray, or matrix-assisted laser desorption (MALDI); gas chromatography (GC); and treatment with exoglycosidases in conjunction with anion-exchange (AIE)-HPLC, size-exclusion chromatography (SEC), mass spectroscopy (MS), gel electrophoresis (SDS-PAGE, CE-PAGE), isoelectric focusing gels, or iso-electric focusing capillary electrophoresis (CE-IEF) See, e.g., Weber et al., *Anal. Biochem.* 225:135 (1995); Klausen et al., *J. Chromatog.* 718:195 (1995); Morris et al., in *Mass Spectrometry of Biological Materials*, McEwen et al., eds., Marcel Dekker, (1990), pp. 137-167; Conboy et al., *Biol. Mass Spectrom.* 21:397, 1992; Hellerqvist, *Meth. Enzymol.* 193:554 (1990); Sutton et al., *Anal. Biohcem.* 318: 34 (1994); Harvey et al., *Organic Mass Spectrometry* 29:752 (1994).

Following resolution of Factor VII-derived oligosaccharide chains using any of the above methods (or any other method that resolves oligosaccharide chains having different structures), the resolved species are assigned, e.g., to one of groups (i)-(vi). The relative content of each of (i)-(vi) is calculated as the sum of the oligosaccharides assigned to that group relative to the total content of oligosaccharide chains in the sample.

For example, using AIE-HPLC, 13 or more N-linked oligosaccharide peaks can be resolved from a recombinant Factor VII preparation produced in BHK cells (see, e.g., Klausen et al., *Mol. Biotechnol.* 9:195, 1998). Five of the peaks (designated 1-5 in Klausen et al.) do not contain sialic acid, while eight of the peaks (designated 6, 7, and 10-15) do contain sialic acid.

It will be understood that, in a given analysis, the number and distribution of sialic acid-containing and sialic acid-lacking chains may depend upon (a) the polypeptide being expressed; (b) the cell type and culture conditions; (c) any modification of glycoform pattern by chemical and/or enzymatic treatment following expression, and (d) the method of analysis that is employed, and that the resulting patterns may vary accordingly.

In any case, once the sialic acid-containing oligosaccharides have been resolved from the non-sialic acid-containing oligosaccharides, conventional data analysis programs are used to calculate the area under each peak; the total peak area; and the percentage of the total peak area represented by a particular peak. In this manner, for a given preparation, the sum of the areas of sialic acid-containing peaks/total peak area×100 yields the % sialylation value for the preparation according to the present invention (i.e., the proportion of oligosaccharide chains having at least one sialic acid residue). In a similar manner, the % of chains having no sialic acid or at least one galactose or N-acetylglucosamine can be calculated.

Polymers

The polymer molecule to be coupled to the polypeptide may be any suitable molecule, such as a natural or synthetic homo-polymer or hetero-polymer, typically with a molecular weight in the range of about 300-100,000 Da, such as about 500-20,000 Da., or about 500-15,000 Da, or 2-15 kDa, or 3-15 kDa, or 3-12 kDa, or about 10 kDa. When the term "about" is used herein in connection with a certain molecular weight the word "about" indicates an approximate average molecular weight distribution in a given polymer preparation.

Examples of homo-polymers include polyalcohols (i.e., poly-OH), polyamines (i.e., poly-NH2) and polycarboxylic acids (i.e., poly-COOH). A hetero-polymer is a polymer comprising different coupling groups such as a hydroxyl group and an amine group.

Examples of suitable polymer molecules include polymer molecules selected from the group consisting of polyalkylene oxide (PAO), including polyalkylene glycol (PAG), such as polyethylene glycol (PEG) and polypropylene glycol (PPG), branched PEGs, polyvinyl alcohol (PVA), polycarboxylate, poly-vinylpyrolidone, polyethylene-co-maleic acid anhydride, polystyrene-co-maleic acid anhydride, dextran, including carboxymethyl-dextran, polyurethaner, polyestre and polyamider, or any other polymer suitable for reducing immunicenicity and/or increasing functional in vivo half-life and/or serum-half-life. Generally, polyalkyleneglycol-derived polymers are biocompatible, non-toxic, non-antigenic, and non-immunogenic, have various water solubility properties, and are easily secreted from living organisms.

PEG is the preferred polymer molecule, since it has only few reactive groups capable of cross-linking compared to, e.g., polysaccharides such as dextran. In particular, monofunctional PEG, e.g., methoxypolyethylene glycol (mPEG) is of interest since its coupling chemistry is relatively simple (only one reactive group is available for conjugating with attachment groups on the oligosaccharide). Consequently, the risk of cross-linking is eliminated, the resulting polypeptide conjugates are more homogeneous and the reaction of the polymer molecules with the polypeptide is easier to control.

To effect covalent attachment of the polymer molecule(s) to the polypeptide, the hydroxyl end groups of the polymer molecule must be provided in activated form, i.e. with reactive functional groups (examples of which include primary amino groups, hydrazide (HZ), thiol, succinate (SUC), succinimidyl succinate (SS), succinimidyl succinamide (SSA), succinimidyl proprionate (SPA), succinimidy carboxymethylate (SCM), benzotriazole carbonate (BTC), N-hydroxysuccinimide (NHS), aldehyde, nitrophenylcarbonate (NPC), and tresylate (TRES)). Suitable activated polymer molecules are commercially available, e.g. from Shearwater Polymers, Inc., Huntsville, Ala., USA, or from PolyMASC Pharmaceuticals plc, UK. Alternatively, the polymer molecules can be activated by conventional methods known in the art, e.g. as disclosed in WO 90/13540. Specific examples of activated linear or branched polymer molecules for use in the present invention are described in the Shearwater Polymers, Inc. 1997 and 2000 Catalogs (Functionalized Biocompatible Polymers for Research and pharmaceuticals, Polyethylene Glycol and Derivatives, incorporated herein by reference).

Specific examples of activated PEG polymers include the following linear PEGs: NHS-PEG (e.g. SPA-PEG, SSPA-PEG, SBA-PEG, SS-PEG, SSA-PEG, SC-PEG, SG-PEG, and SCM-PEG), and NOR-PEG, BTC-PEG, EPOX-PEG, NCO-PEG, NPC-PEG, CDI-PEG, ALD-PEG, TRES-PEG, VS-PEG, IODO-PEG, and MAL-PEG, and branched PEGs such as PEG2-NHS and those disclosed in U.S. Pat. No. 5,932,462 and U.S. Pat. No. 5,643,575, both of which are incorporated herein by reference. Furthermore, the following publications, incorporated herein by reference, disclose useful polymer molecules and/or PEGylation chemistries: U.S. Pat. No. 5,824,778, U.S. Pat. No. 5,476,653, WO 97/32607, EP 229,108, EP 402,378, U.S. Pat. No. 4,902,502, U.S. Pat. No. 5,281,698, U.S. Pat. No. 5,122,614, U.S. Pat. No. 5,219,564, WO 92/16555, WO 94/04193, WO 94/14758, WO 94/17039, WO 94/18247, WO 94/28024, WO 95/00162, WO 95/11924, WO95/13090, WO 95/33490, WO 96/00080, WO 97/18832, WO 98/41562, WO 98/48837, WO 99/32134, WO 99/32139, WO 99/32140, WO 96/40791, WO 98/32466, WO 95/06058, EP 439 508, WO 97/03106, WO 96/21469, WO 95/13312, EP 921 131, U.S. Pat. No. 5,736,625, WO 98/05363, EP 809 996, U.S. Pat. No. 5,629,384, WO 96/41813, WO 96/07670, U.S. Pat. No. 5,473,034, U.S. Pat. No. 5,516,673, EP 605 963, U.S. Pat. No. 30 5,382,657, EP 510 356, EP 400 472, EP 183 503 and EP 154 316.

The conjugation of the oligosaccharide chains of the polypeptide and the activated polymer molecules is conducted by use of any conventional method. Conventional methods are known to the skilled artisan.

The skilled person will be aware that the activation method and/or conjugation chemistry to be used depends on the attachment group(s) of the oligosaccharide(s) as well as the functional groups of the polymer molecule (e.g., being amine, hydroxyl, carboxyl, aldehyde, ketone, sulfhydryl, succinimidyl, maleimide, vinylsulfone or haloacetate).

It will be understood that the polymer conjugation is designed so as to produce the optimal molecule with respect to the number of polymer molecules attached, the size and form of such molecules (e.g., whether they are linear or branched), and the attachment site(s) in the oligosaccharide chain(s). The molecular weight of the polymer to be used may e.g., be chosen on the basis of the desired effect to be achieved. For instance, if the primary purpose of the conjugation is to achieve a conjugate having a high molecular weight (e.g., to reduce renal clearance) it is usually desirable to conjugate as few high molecular weight polymer molecules as possible to obtain the desired molecular weight.

It is also contemplated according to the invention to couple the polymer molecules to the polypeptide through a linker. Suitable linkers are well known to the skilled person. A preferred example is cyanuric chloride (Abuchowski et al., (1977), J. Biol. Chem., 252, 3578-3581; U.S. Pat. No. 4,179, 337; Shafer et al., (1986), J. Polym. Sci. Polym. Chem. Ed., 24, 375-378). Subsequent to the conjugation, residual activated polymer molecules are blocked according to methods known in the art, e.g. by addition of primary amine to the reaction mixture, and the resulting inactivated polymer molecules are removed by a suitable method. Such methods are well known to the skilled person; see, e.g., March, *Advanced Organic Chemistry*, 3$^{rd}$ edition, John Wiley & Sons, N.Y. 1985; Greene et al., *Protective groups in Organic Synthesis*, John Wiley & Sons, N.Y., 1991; Taylor (1991), *Protein Immobilization, Fundamentals and Applications*, Marcel Dekker, N.Y.; Wong (1992), *Chemistry of protein Conjugation and Crosslinking*, CRC Press, Boca Raton; Hermanson et al., (1993), *Immobilized Affinity Ligand Techniques*, Academic Press, N.Y.; Dunn et al., Eds. *Polymeric Drugs and Drug Delivery Systems*, ACS Symposium Series Vol. 469, American Chemical Society, 1991.)

It will be understood that depending on the circumstances, e.g. the amino acid sequence of the polypeptide, the nature of the activated PEG compound being used and the specific PEGylation conditions, including the molar ratio of PEG to polypeptide, varying degrees of PEGylation may be obtained, with a higher degree of PEGylation generally being obtained with a higher ratio of PEG to polypeptide. The PEGylated polypeptides resulting from any given PEGylation process will, however, normally comprise a stochastic distribution of polypeptide conjugates having slightly different degrees of PEGylation.

In an interesting embodiment of the invention the polypeptide conjugate of the present invention comprises a polymer molecule covalently attached to one of the sialic acid groups located at the terminal end of a oligosaccharide group of a Factor VII polypeptide, where said polymer molecule is the only polymer molecule attached to the polypeptide. In another embodiment, two polymer molecules are covalently bound to one or more oligosaccharide group(s) of the Factor VII polypeptide; in other embodiments, three, four, five, six, or seven polymer molecules are covalently attached to the Factor VII polypeptide.

In one embodiment, the Factor VII polypeptide is the wildtype FVII or FVIIa polypeptide shown in FIG. 1; in another embodiment, the Factor VII polypeptide is a Factor VII-related polypeptide; in one embodiment thereof, the Factor VII-related polypeptide is a Factor VII amino acid sequence variant.

Preferably, such polypeptide conjugates are ones, which comprise a single PEG molecule. In particular, a linear or branched PEG molecule with a molecular weight of at least about 5 kDa, in particular about 10-25 kDa, such as about 15-25 kDa, e.g. about 20 kDa or about 10 kDa is preferred.

Preferably, in a conjugate of the invention the number and molecular weight of the polymeric molecule is chosen so as that the total molecular weight added by the polymeric molecule is in the range of 5-25 kDa, such as, e.g., in the range of 10-25 kDa, about 5 kDa, about 10 kDa, about 15 kDa, or about 20 kDa.

Methods for Producing Polymer-Attached Factor VII Preparations Having a Predetermined Pattern of Oligosaccharides Methods for producing Factor VII Preparations: Factor VII, Factor VII variants, or Factor VII-related polypeptides, may be produced using any appropriate host cell that expresses glycosylated Factor VII or Factor VII-related polypeptides (i.e., host cells capable of attaching oligosaccharide groups at the glycosylation sites of the polypeptide). Factor VII may also be isolated from plasma from humans or other species.

In some embodiments, the host cells are human cells expressing an endogenous Factor VII gene. In these cells, the endogenous gene may be intact or may have been modified in situ, or a sequence outside the Factor VII gene may have been modified in situ to alter the expression of the endogenous Factor VII gene. Any human cell capable of expressing an endogenous Factor VII gene may be used.

In other embodiments, heterologous host cells are programmed to express human Factor VII from a recombinant gene. The host cells may be vertebrate, insect, or fungal cells. Preferably, the cells are mammalian cells capable of the entire spectrum of mammalian N-linked glycosylation; O-linked glycosylation; and γ-carboxylation. See, e.g., U.S. Pat. No. 4,784,950. Preferred mammalian cell lines include the CHO (ATCC CCL 61), COS-1 (ATCC CRL 1650), baby hamster kidney (BHK) and HEK293 (ATCC CRL 1573; Graham et al., *J. Gen. Virol.* 36:59-72, 1977) cell lines. A preferred BHK cell line is the tk$^-$ ts13 BHK cell line (Waechter and Baserga, *Proc. Natl. Acad. Sci. USA* 79:1106-1110, 1982), hereinafter referred to as BHK 570 cells. The BHK 570 cell line is available from the American Type Culture Collection, 12301 Parklawn Dr., Rockville, Md. 20852, under ATCC accession number CRL 10314. A tk$^-$ ts13 BHK cell line is also available from the ATCC under accession number CRL 1632. In addition, a number of other cell lines may be used, including Rat Hep I (Rat hepatoma; ATCC CRL 1600), Rat Hep II (Rat hepatoma; ATCC CRL 1548), TCMK (ATCC CCL 139), Human lung (ATCC HB 8065), NCTC 1469 (ATCC CCL 9.1) and DUKX cells (CHO cell line) (Urlaub and Chasin, *Proc. Natl. Acad. Sci. USA* 77:4216-4220, 1980). (DUKX cells also referred to as CXB11 cells), and DG44 (CHO cell line) (*Cell*, 33:405, 1983, and *Somatic Cell and Molecular Genetics* 12:555, 1986). Also useful are 3T3 cells, Namalwa cells, myelomas and fusions of myelomas with other cells. In a particularly preferred embodiment, the host cells are BHK 21 cells that have been adapted to grow in the absence of serum and have been programmed to express Factor VII. In some embodiments, the cells may be mutant or recombinant cells that express a qualitatively or quantitatively different spectrum of glycosylation enzymes (such as, e.g., glycosyl transferases and/or glycosidases) than the cell type from which they were derived. The cells may also be programmed to express other heterologous peptides or proteins, including, e.g., truncated forms of Factor VII. In one embodiment, the host cells are CHO cells that have been programmed to co-express both the Factor VII polypeptide of interest (i.e., Factor VII or a Factor-VII-related polypeptide) and another heterologous peptide or polypeptide such as, e.g., a modifying enzyme or a Factor VII fragment.

The methods for producing a preparation of Factor VII comprising any of the glycoform patterns described above as (i)-(vi) and methods for optimizing the glycoform distribution of Factor VII and Factor VII-related polypeptides may be carried out by the steps of:

(a) culturing a cell expressing Factor VII or Factor VII-related polypeptides under a first set of predetermined culture conditions;

(b) recovering Factor VII or Factor VII-related polypeptides from the culture to obtain a preparation comprising the polypeptides; and (c) analyzing the structure of the oligosaccharides linked to the polypeptides to determine a glycoform pattern.

The methods may further comprise:

(d1) altering the culture conditions of step (a) to achieve a second set of predetermined culture conditions;

(e1) repeating steps (b)-(d1) until a desired glycoform pattern is achieved;

(f1) contacting the Factor VII or Factor VII-related polypeptides with a polymer molecule under conditions in which the polymer molecule is covalently attached to the oligosaccharide group of the polypeptide.

Alternatively, the methods may further comprise (d2) treating the preparation chemically and/or enzymatically to alter the oligosaccharide structure; and (e2) repeating steps (b)-(d2) until a desired glycoform pattern is achieved.

These methods may further comprise the step of subjecting preparations having predetermined glycoform patterns to at least one test of bioactivity (including, e.g., clotting, Factor X proteolysis, or TF binding) or other functionality (such as, e.g., pharmacokinetic profile or stability), and correlating particular glycoform patterns with particular bioactivity or functionality profiles in order to identify a desired glycoform pattern.

The variables in the culture conditions that may be altered in step (d1) include, without limitation: the cell of origin, such as, e.g., a cell derived from a different species than originally used; or a mutant or recombinant cell having alterations in one or more glycosyltransferases or glycosidases or other components of the glycosylation apparatus (see, Grabenhorst et al., *Glycoconjugate J.* 16:81, 1999; Bragonzi et al., *Biochem. Biophys. Acta* 1474:273, 2000; Weikert, *Nature Biotechnol.* 17:1116, 1999); the level of expression of the polypeptide; the metabolic conditions such as, e.g., glucose or glutamine concentration; the absence or presence of serum; the concentration of vitamin K; protein hydrolysates, hormones, trace metals, salts as well as process parameters like temperature, dissolved oxygen level and pH.

The enzymatic treatments that may be used in step (d2) to modify the oligosaccharide pattern of a preparation include, without limitation, treatment with one or more of sialidase (neuraminidase), galactosidase, fucosidase; galactosyl transferase, fucosyl transferase, and/or sialyltransferase, in a sequence and under conditions that achieve a desired modification in the distribution of oligosaccharide chains having particular terminal structures. Glycosyl transferases are commercially available from Calbiochem (La Jolla, Calif.) and glycosidases are commercially available from Glyko, Inc., (Novato, Calif.).

In one series of embodiments, host cells expressing Factor VII or a related polypeptide are subjected to specific culture conditions in which they secrete glycosylated Factor VII polypeptides having the desired pattern of oligosaccharide structures described above as any of (i)-(vi). Such culture conditions include, without limitation, a reduction in, or complete absence of, serum. Preferably, the host cells are adapted to grow in the absence of serum and are cultured in the absence of serum both in the growth phase and in the production phase. Such adaptation procedures are described, e.g., in Scharfenberg, et al., *Animal Cell Technology Developments towards the 21st Century*, E. C. Beuvery et al. (Eds.), Kluwer Academic Publishers, pp. 619-623, 1995 (BHK and CHO cells); Cruz, *Biotechnol. Tech.* 11:117-120, 1997 (insect cells); Keen, *Cytotechnol.* 17:203-211, 1995 (myeloma cells); Berg et al., *Biotechniques* 14:972-978, 1993 (human kidney 293 cells). In a preferred embodiment, the growth medium that is added to the cells contains no protein or other component that was isolated from an animal tissue or an animal cell culture. See, e.g., Example 1 below. Typically, in addition to conventional components, a medium suitable for producing Factor VII contains Vitamin K at a concentration between 0.1-50 mg/liter, which is required for γ-carboxylation of glutamine residues in Factor VII.

In another series of embodiments, the glycoforms are produced by subjecting a preparation of Factor VII or Factor VII-related polypeptides to enzymatic and/or chemical modification of the N-linked and/or O-linked oligosaccharides contained therein, such as subjecting the preparation to modification by a sialyltransferase or a galactosyl transferase, such as described, e.g. in U.S. Pat. No. 6,399,336. Preferably, the N-linked oligosaccharides are modified. A sialyltransferase is capable of sialylating a high percentage of acceptor groups (e.g., terminal galactose) on a glycoprotein. The desired result is usually obtained by using about 50 mU of sialyltransferase per mg of glycoprotein or less. Typically, the oligosaccharide chains on a glycoprotein having their glycoform patterns altered by this method, will as a result have a greater percentage of terminal galactose residues sialylated than the unaltered polypeptide. Essentially, 100% percent of the terminal galactose residues may be sialylated following use of these methods. The methods are typically capable of achieving the desired level of sialylation in about 48 hours or less. Preferably, for glycosylation of N-linked carbohydrates of glycoproteins the sialyltransferase will be able to transfer sialic acid to the sequence Gal(β1→4)GlcNAc-, the most common penultimate sequence underlying the terminal sialic acid on fully sialylated carbohydrate structures. Examples of sialyltransferases that use Gal(β1→4)GlcNAc- as an acceptor group are ST3Gal III, ST3Gal IV, and ST3Gal V (attach NeuAc by an α2→3 linkage) and ST6Gal I and ST6Gal II (attach NeuAc by an α2→6 linkage) (see U.S. Pat. No. 6,399,336). (Sialyltransferase nomenclature is described in Tsuji et al., *Glycobiology* 6:v-xiv (1996)).

Thus, a mixture of the two enzymes may be of value if both linkages are desired in the final product. In short, the silaylation of the glycoprotein is accomplished using, for example, a sialyltransferase cycle, which includes a CMP-sialic acid synthetase. The CMP-regenerating system in this cycle comprises cytidine monophosphate (CMP), a nucleoside triphosphate, a phosphate donor, a kinase capable of transferring phosphate from the phosphate donor to the nucleoside diphosphates and a nucleoside monophosphate kinase capable of transferring the terminal phosphate from a nucleoside triphosphate to CMP. The regenerating system also employs CMP-sialic acid synthetase, which transfers sialic acid to CMP. In the sialylation cycle, CMP is converted to CDP by nucleoside monophosphate kinase in the presence of added ATP. ATP is catalytically regenerated from its byproduct, ADP, by pyruvate kinase (PK) in the presence of added phosphoenolpyruvate (PEP). CDP is further converted to CTP, which conversion is catalyzed by PK in the presence of PEP. CTP reacts with sialic acid to form inorganic pyrophosphate (PPi) and CMP-sialic acid, the latter reaction being catalyzed by CMP-sialic acid synthetase. Following sialylation of the galactosyl glucoside, the released CMP re-enters the regenerating system to form CDP, CTP and CMP-sialic acid. The formed PPi is scavenged and forms inorganic phosphate as a byproduct. Pyruvate is also a byproduct. Because of the self-contained and cyclic character of the method, once all the reactants and enzymes are present, the reaction continues until the first of the substrates (e.g., free NeuAc and PEP, or the acceptor) is consumed. Sialyltransferase cycles are described e.g., in U.S. Pat. No. 5,374,541 and U.S. Pat. No. 6,399,336.

Acceptors for the sialyltransferase will be present on the glycoprotein to be modified. Suitable acceptors include, for example, Gal(β1→4)GlcNAc-, Gal(β1→4)GalNAc-, Gal(β1→3)GalNAc-, Gal(β1→3)GlcNAc-, Gal(β1→6)GlcNAc-, Gal(β1→4)Glc- and other acceptors known to those skilled in the art (see, e.g., Paulson et al. (1978) *J. Biol. Chem.* 253: 5617-5624). Typically, the receptors are included in the oligosaccharide chains that are attached to asparagine, serine or threonine residues present in a polypeptide.

The glycoprotein may be "trimmed", either whole or in part, to expose either an acceptor for the sialyltransferase, or a moiety to which one or more appropriate residues can be added to obtain a suitable acceptor. Enzymes such as glycosyltransferases and endoglycosidases are useful for the attaching and trimming reactions. By example, the glycoprotein may be "trimmed" by treating it with sialidase to create terminal galactose groups before subjecting the protein to a sialyltransferase cycle, or even further down to the N-acetylglucosamine level by further treatment with galactosidases. See, e.g., U.S. Pat. No. 5,272,066 for methods of obtaining polypeptides having suitable acceptors for sialylation.

Methods for Covalently Attaching Polymer Molecules to the Factor VII Polypeptides:

Various chemical moieties such as the polymer molecules used in working the present invention can be covalently attached to the oligosaccharides on the Factor VII polypeptide by either chemical synthesis or enzymatic treatment of the polypeptide with, e.g., modified sialic acid. The polymer molecule may also be coupled to the oligosaccharide through a linker. Suitable linkers are well known to the skilled person Examples include but are not limited to N-(4-acetylphenyl) mailmide, succimidyl ester activatede malimido derivatives such as commercial available succimidyl 4-malimidobutanoate, 1,6-bismalimidohexanes.

Various chemical moieties such as the polymer molecules used in working the present invention can be covalently attached to the sialic acid and the thus "modified" (or conjugated) sialic acid subsequently incorporated in the sialyltransferase cycle resulting in the polymer molecule being covalently attached to the glycoprotein. The conjugated sialic acid can be made by conventional methods known by the skilled artisan. The polymer molecule may also be coupled to the sialic acid through through a linker.

Chemoenzymatic Derivatisation of FVII and FVII Analogues

The modified sugar phospho nucleotides of use in practicing the present invention can be substituted according to general formula I and II:

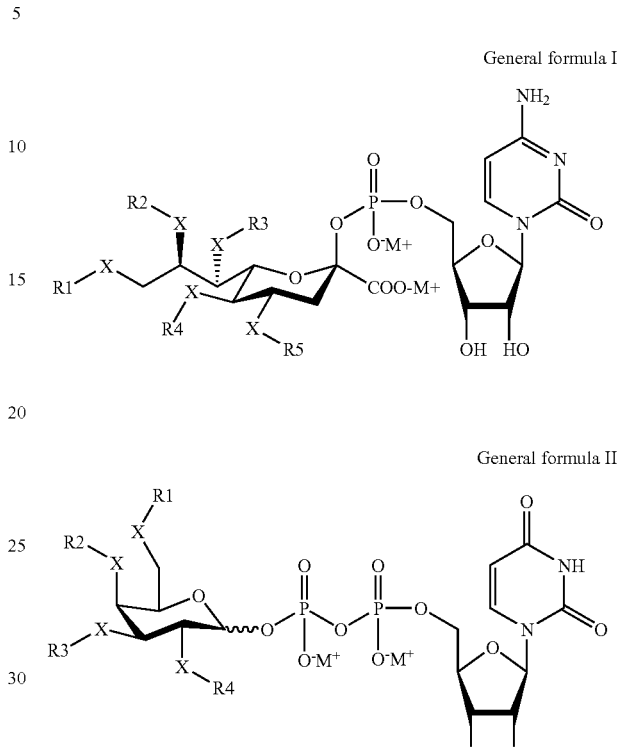

Wherein
X are members independently selected from S, O, NH, or a valence bond;
R1, R2, R3, R4 and R5 are a members independently selected from H, a polymer and linker molecule covalently attached to a polymer, acyl (including acetyl and hydroxyacetyl), and alkyl;
M+ is a cation selected from Na+, K+, Li+, tetrabutyl ammonium or similar cation.

In a preferred embodiment, R1 and R2 is independently a PEG-based polymer with a mass of 1-40.000 kDa.

In a still more preferred embodiment, R1 is independently a PEG-based polymer with a mass of 1-40.000 kDa.

In an exemplary embodiment, set forth in Scheme 1, amine-, 2-hydroxy- and carboxyl protected neuraminic acid is initially converted in to its 9-amino derivative according to Isecke, R.; Brossmer, R., *Tetrahedron* 1994, 50(25), 7445-7460, which is further derivatized with PEG-COOH using standard coupling conditions. The PEG derivatized product is then deprotected under mild acid conditions, and enzymatically converted into the corresponding nucleotide sugar.

Scheme 1:

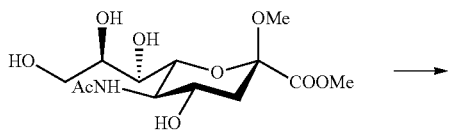

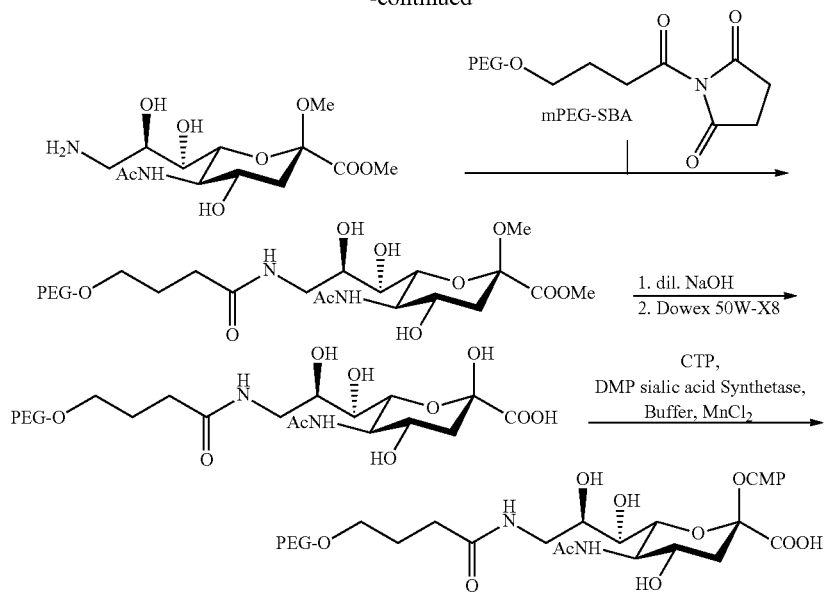

In another exemplary embodiment, set forth in Scheme 2, N-acetyl neuraminic acid is treated with PEG-derivatised thioacids under Mitsunobu conditions, to give a PEG-derivatized N-acetyl neuraminic acid that subsequently is converted into a sugar nucleotide.

Scheme 2:

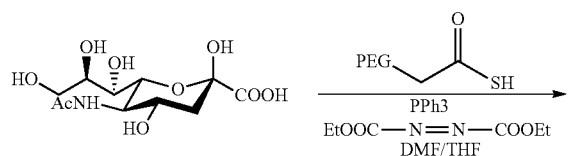

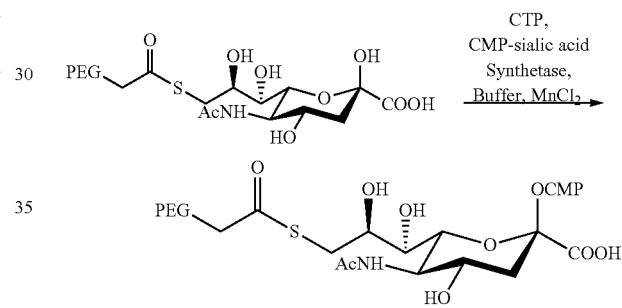

In an exemplary embodiment, set forth in Scheme 3, the thiol of a modified galactose reacts with a PEG containing a maleimide moiety. The PEG-galactose compound can then be converted to the corresponding nucleotide sugar by either enzymatic or chemical methods.

Scheme 3

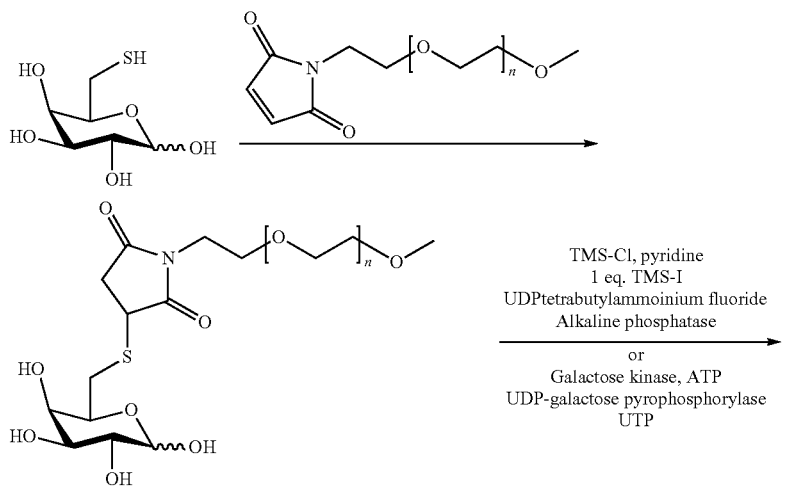

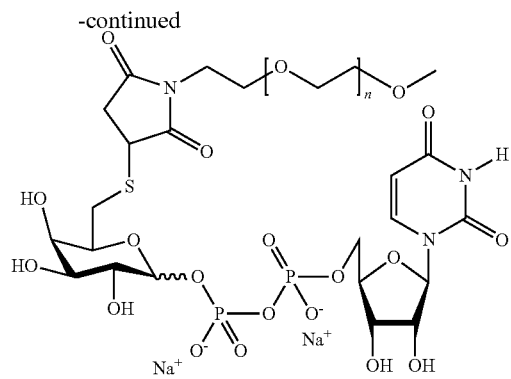

In another exemplary embodiment set forth in Scheme 4, 6-amino galactose (Fernandez, J. et al., *J. Org. Chem.* 1993, 58(19), 5192-5199) reacts with a PEG containing an protected amino acid moiety. The methyl ester is saponified. The PEG-galactose compound can then be converted to the corresponding nucleotide sugar by either enzymatic or chemical methods.

In another exemplary embodiment set forth in Scheme 5, a protected 6-bromo-galactose (Hodosi, G., Podanyi, B. and Kuszmann, J., *Carbohydr. Res.*, 1992, 230(2), 327-342) reacts with a PEG containing a thiol moiety. The isopropylidene groups are removed under acidic conditions. The PEG-galactose compound can then be converted to the corresponding nucleotide sugar by either enzymatic or chemical methods.

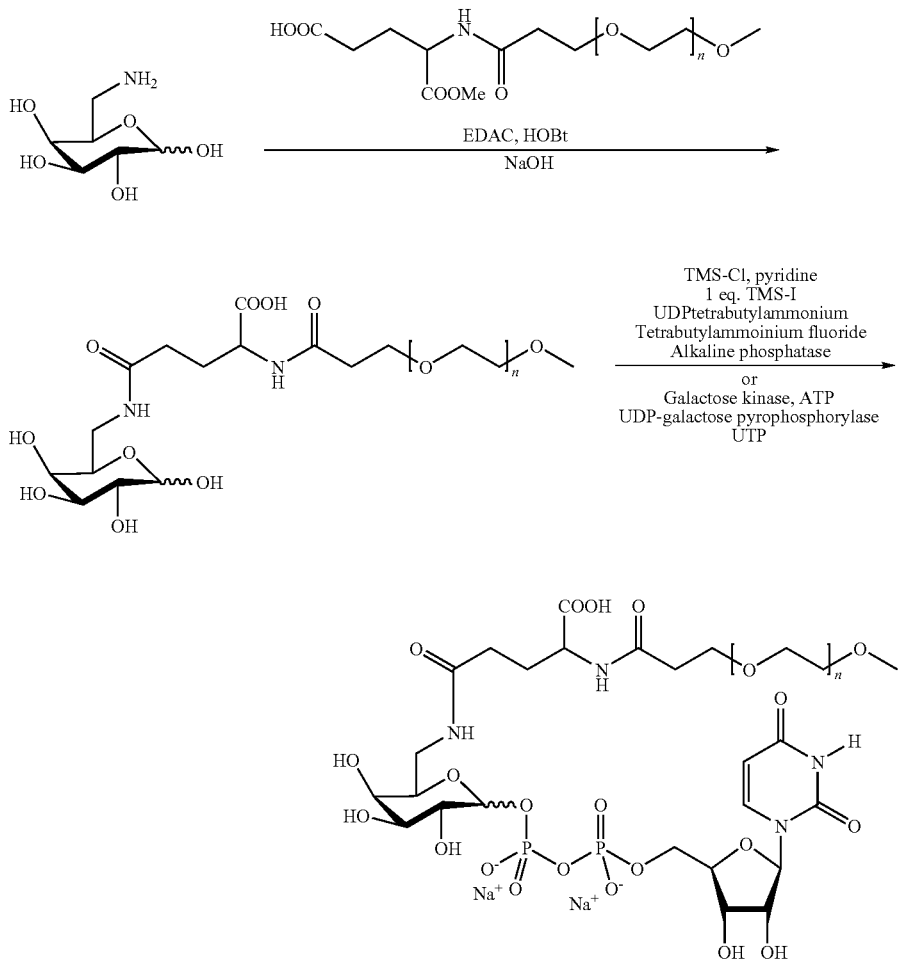

Scheme 4

Scheme 5

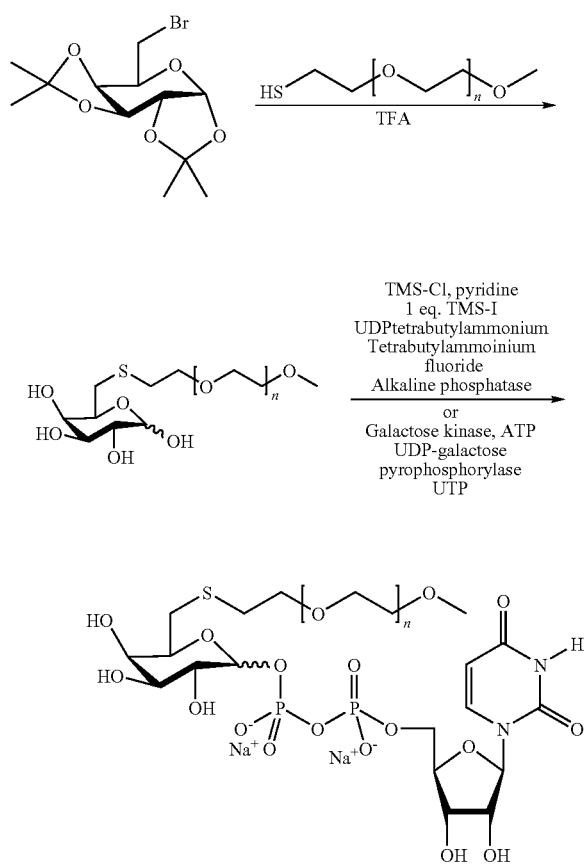

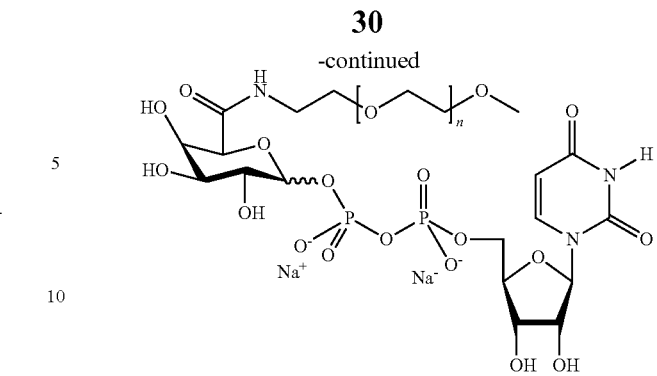

In another exemplary embodiment set forth in Scheme 6, a protected galacturonic acid (Godage, Y. S, and Fairbanks, A. J., *Tetrahedron Lett.*, 2000, 41(39), 7589-7594) reacts with a PEG containing an amine moiety. The isopropylidene groups are removed under acidic conditions. The PEG-galactose compound can then be converted to the corresponding nucleotide sugar by either enzymatic or chemical methods.

Scheme 6

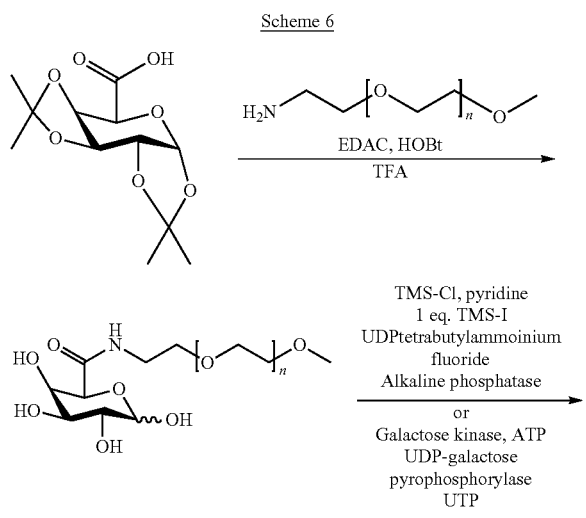

In general, sugar nucleotides such as those described above can be enzymatically transferred on to suitable glycoproteins, such as FVII or FVII-related polypeptide, using natural or mutated glycosyl transferases, which includes by illustration but not limitation: α2,3-sialyl transferases, α2,6-sialyl transferases or 1,4-galactosyl transferases. Depending of the choice of PEG-derivatised sugar nucleotide (CMP-SA-PEG or UDP-Gal-PEG), it may be preferably to treat the FVII-related polypeptide with sialidase, galactosidase or both, prior to the reaction with glycosyl transferases and PEG-derivatised sugar nucleotide.

Thus in one preferred embodiment, a FVII analogue is treated with sialidase, to produce an asialo FVII analogue, that subsequently is treatment with sialyltransferase and a CMP-SA-PEG analogue according to general formula I, to give a PEG-derivatised FVII analogue.

In another embodiment, a FVII-related polypeptide is treated sequentially first with sialidase and secondly with galactosidase, to produce an asialo agalacto FVII-related polypeptide. This analogue is then treated with galactosyltransferase and an UDP-Gal-PEG analogue according to general formula II, to give a PEG-derivatised FVII analogue.

In series of embodiments, modified galactose compounds, which are covalently bound to a polymer either directly or using a linker moiety are employed. One can either employ the Factor VII or Factor VII-related polypeptides directly to obtain lower levels of polymer per polypeptide or first treat the Factor VII or Factor VII-related polypeptides with a sialidase, to remove the terminal sialic acids in order to obtain higher levels of polymer per peptide. By treating the polypeptide with a galactosidase, the attachment points for the modified galactose compounds are accessed. The bond between the modified galactose compounds and the treated polypeptide can be formed by employing the UDP activated form of the modified galactose compounds and a galactosyltransferase. An exemplary embodiment of this type is illustrated in Scheme 7, in which the black circle represents Factor VII or Factor VII-related polypeptides, and the terminal portion of a few of the carbohydrates are illustrated.

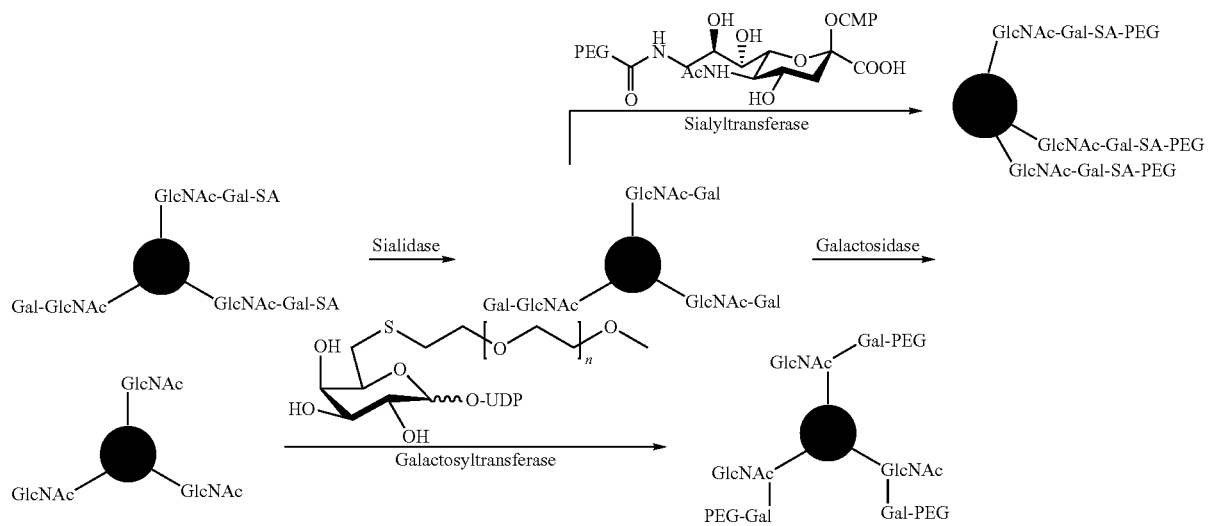

Scheme 7

Chemical Derivatisation of FVII and FVII Analogues

Chemical oxidation of carbohydrate residues using sodium periodate is an alternative method for preparation of FVII-PEG conjugates. Chemical oxidation of carbohydrate will generally generate multiple of reactive aldehyde groups, each capable of reacting with PEG-nucleophiles such as PEG-hydrazide, PEG-O-hydroxylamine and PEG-amine.

With PEG-hydrazide and PEG-O-hydroxylamine respectively, stable FVII-PEG-acylhydrazone and FVII-PEG-oxime conjugates can be prepared. With PEG-amines, a less stable Shiff base conjugate forms. This conjugate however can be further stabilized by reduction with sodium cyanoborohydride, whereby a secondary amine linkage is formed. FVII-PEG-acylhydrazone conjugates also can be reduced with sodiumcyanoborohydride whereby N,N' linked hydrazine conjugates are formed.

Purification of Glyco-Conjugated Factor VII Preparations

As used herein, a "Factor VII preparation" refers to a plurality of Factor VII polypeptides, Factor VIIa polypeptides, or Factor VII-related polypeptides, including variants and chemically modified forms, that have been separated from the cell or reaction medium in which they were synthesized.

Purification of Factor VII Preparations and Conjugates:

Separation of recombinantly produced polypeptides from their cell of origin may be achieved by any method known in the art, including, without limitation, removal of cell culture medium containing the desired product from an adherent cell culture; centrifugation or filtration to remove non-adherent cells; and the like.

Optionally, Factor VII polypeptides may be further purified. Purification may be achieved using any method known in the art, including, without limitation, affinity chromatography, such as, e.g., on an anti-Factor VII antibody column (see, e.g., Wakabayashi et al., J. Biol. Chem. 261:11097, 1986; and Thim et al., Biochem. 27:7785, 1988); hydrophobic interaction chromatography; ion-exchange chromatography; size exclusion chromatography; electrophoretic procedures (e.g., preparative isoelectric focusing (IEF), differential solubility (e.g., ammonium sulfate precipitation), or extraction and the like. See, generally, Scopes, Protein Purification, Springer-Verlag, New York, 1982; and Protein Purification, J.-C. Janson and Lars Ryden, editors, VCH Publishers, New York, 1989. Following purification, the preparation preferably contains less than about 10% by weight, more preferably less than about 5% and most preferably less than about 1%, of non-Factor VII proteins derived from the host cell.

Factor VII and Factor VII-related polypeptides may be activated by proteolytic cleavage, using Factor XIIa or other proteases having trypsin-like specificity, such as, e.g., Factor IXa, kallikrein, Factor Xa, and thrombin. See, e.g., Osterud et al., Biochem. 11:2853 (1972); Thomas, U.S. Pat. No. 4,456, 591; and Hedner et al., J. Clin. Invest. 71:1836 (1983). Alternatively, Factor VII may be activated by passing it through an ion-exchange chromatography column, such as Mono Q® (Pharmacia) or the like. The resulting activated Factor VII may then be formulated and administered as described below.

Functional Properties of Factor VII Preparations

The preparations according to the invention of Factor VII polypeptides and Factor VII-related polypeptides having predetermined oligosaccharide patterns with covalently attached polymer molecules exhibit improved functional properties relative to reference preparations. The improved functional properties may include, without limitation, a) physical properties such as, e.g., storage stability; b) pharmacokinetic properties such as, e.g., bioavailability and half-life; and c) immunogenicity in humans.

A reference preparation refers to a preparation comprising a polypeptide that has an amino acid sequence identical to that contained in the preparation of the invention to which it is being compared (such as, e.g., non-conjugated forms of wild-type Factor VII or a particular variant or chemically modified form) but which is not conjugated to any polymer molecule(s) found in the preparation of the invention. For example, reference preparations typically comprise non-conjugated wild-type Factor VII or non-conjugated Factor VII-related polypeptides.

Storage stability of a Factor VII preparation may be assessed by measuring (a) the time required for 20% of the bioactivity of a preparation to decay when stored as a dry powder at 25° C. and/or (b) the time required for a doubling in the proportion of Factor VIIa aggregates in the preparation.

In some embodiments, the preparations of the invention exhibit an increase of at least about 30%, preferably at least about 60% and more preferably at least about 100%, in the time required for 20% of the bioactivity to decay relative to the time required for the same phenomenon in a reference preparation, when both preparations are stored as dry powders at 25° C. Bioactivity measurements may be performed using any of a clotting assay, proteolysis assay, TF-binding assay, or TF-independent thrombin generation assay.

In some embodiments, the preparations of the invention exhibit an increase of at least about 30%, preferably at least about 60%, and more preferably at least about 100%, in the time required for doubling of aggregates relative to a reference preparation, when both preparations are stored as dry powders at 25° C. The content of aggregates is determined by gel permeation HPLC on a Protein Pak 300 SW column (7.5×300 mm) (Waters, 80013) as follows. The column is equilibrated with Eluent A (0.2 M ammonium sulfate, 5% isopropanol, pH adjusted to 2.5 with phosphoric acid, and thereafter pH is adjusted to 7.0 with triethylamine), after which 25 µg of sample is applied to the column. Elution is with Eluent A at a flow rate of 0.5 ml/min for 30 min, and detection is achieved by measuring absorbance at 215 nm. The content of aggregates is calculated as the peak area of the Factor VII aggregates/total area of Factor VII peaks (monomer and aggregates).

"Bioavailability" refers to the proportion of an administered dose of a Factor VII or Factor VII-related preparation that can be detected in plasma at predetermined times after administration. Typically, bioavailability is measured in test animals by administering a dose of between about 25-250 µg/kg of the preparation; obtaining plasma samples at predetermined times after administration; and determining the content of Factor VII or Factor VII-related polypeptides in the samples using one or more of a clotting assay (or any bioassay), an immunoassay, or an equivalent. The data are typically displayed graphically as [Factor VII] v. time and the bioavailability is expressed as the area under the curve (AUC). Relative bioavailability of a test preparation refers to the ratio between the AUC of the test preparation and that of the reference preparation.

In some embodiments, the preparations of the present invention exhibit a relative bioavailability of at least about 110%, preferably at least about 120%, more preferably at least about 130% and most preferably at least about 140% of the bioavailability of a reference preparation. The bioavailability may be measured in any mammalian species, preferably dogs, and the predetermined times used for calculating AUC may encompass different increments from 10 min-8 h.

"Half-life" refers to the time required for the plasma concentration of Factor VII polypeptides of Factor VII-related polypeptides to decrease from a particular value to half of that value. Half-life may be determined using the same procedure as for bioavailability. In some embodiments, the preparations of the present invention exhibit an increase in half-life of at least about 0.25 h, preferably at least about 0.5 h, more preferably at least about 1 h, and most preferably at least about 2 h, relative to the half-life of a reference preparation.

"Immunogenicity" of a preparation refers to the ability of the preparation, when administered to a human, to elicit a deleterious immune response, whether humoral, cellular, or both. Factor VIIa polypeptides and Factor VIIa-related polypeptides are not known to elicit detectable immune responses in humans. Nonetheless, in any human sub-population, there may exist individuals who exhibit sensitivity to particular administered proteins. Immunogenicity may be measured by quantifying the presence of anti-Factor VII antibodies and/or Factor VII-responsive T-cells in a sensitive individual, using conventional methods known in the art. In some embodiments, the preparations of the present invention exhibit a decrease in immunogenicity in a sensitive individual of at least about 10%, preferably at least about 25%, more preferably at least about 40% and most preferably at least about 50%, relative to the immunogenicity for that individual of a reference preparation.

Pharmaceutical Compositions

The preparations of the present invention may be used to treat any Factor VII-responsive syndrome, such as, e.g., bleeding disorders, including, without limitation, those caused by clotting factor deficiencies (e.g., haemophilia A and B or deficiency of coagulation factors XI or VII); by thrombocytopenia or von Willebrand's disease, or by clotting factor inhibitors, or excessive bleeding from any cause. The preparations may also be administered to patients in association with surgery or other trauma or to patients receiving anticoagulant therapy.

Preparations comprising Factor VII-related polypeptides according to the invention, which have substantially reduced bioactivity relative to wild-type Factor VII, may be used as anticoagulants, such as, e.g., in patients undergoing angioplasty or other surgical procedures that may increase the risk of thrombosis or occlusion of blood vessels as occurs, e.g., in restenosis. Other medical indications for which anticoagulants are prescribed include, without limitation, deep vein thrombosis, pulmonary embolism, stroke, disseminated intravascular coagulation (DIC), fibrin deposition in lungs and kidneys associated with gram-negative endotoxemia, myocardial infarction; Acute Respiratory Distress Syndrome (ARDS), Systemic Inflammatory Response Syndrome (SIRS), Hemolytic Uremic Syndrome (HUS), MOF, and TTP.

Pharmaceutical compositions comprising the Factor VII and Factor VII-related preparations according to the present are primarily intended for parenteral administration for prophylactic and/or therapeutic treatment. Preferably, the pharmaceutical compositions are administered parenterally, i.e., intravenously, subcutaneously, or intramuscularly. They may be administered by continuous or pulsatile infusion.

Pharmaceutical compositions or formulations comprise a preparation according to the invention in combination with, preferably dissolved in, a pharmaceutically acceptable carrier, preferably an aqueous carrier or diluent. A variety of aqueous carriers may be used, such as water, buffered water, 0.4% saline, 0.3% glycine and the like. The preparations of the invention can also be formulated into liposome preparations for delivery or targeting to the sites of injury. Liposome preparations are generally described in, e.g., U.S. Pat. Nos. 4,837,028, 4,501,728, and 4,975,282. The compositions may be sterilised by conventional, well-known sterilisation techniques. The resulting aqueous solutions may be packaged for use or filtered under aseptic conditions and lyophilised, the lyophilised preparation being combined with a sterile aqueous solution prior to administration.

The compositions may contain pharmaceutically acceptable auxiliary substances or adjuvants, including, without limitation, pH adjusting and buffering agents and/or tonicity adjusting agents, such as, for example, sodium acetate, sodium lactate, sodium chloride, potassium chloride, calcium chloride, etc.

The concentration of Factor VII or Factor VII-related polypeptides in these formulations can vary widely, i.e., from less than about 0.5% by weight, usually at or at least about 1% by weight to as much as 15 or 20% by weight and will be selected primarily by fluid volumes, viscosities, etc., in accordance with the particular mode of administration selected.

Thus, a typical pharmaceutical composition for intravenous infusion could be made up to contain 250 ml of sterile Ringer's solution and 10 mg of the preparation. Actual methods for preparing parenterally administrable compositions will be known or apparent to those skilled in the art and are described in more detail in, for example, *Remington's Pharmaceutical Sciences*, 18th ed., Mack Publishing Company, Easton, Pa. (1990).

The compositions containing the preparations of the present invention can be administered for prophylactic and/or therapeutic treatments. In therapeutic applications, compositions are administered to a subject already suffering from a disease, as described above, in an amount sufficient to cure, alleviate or partially arrest the disease and its complications. An amount adequate to accomplish this is defined as "therapeutically effective amount". Effective amounts for each purpose will depend on the severity of the disease or injury as well as the weight and general state of the subject. In general, however, the effective amount will range from about 0.05 mg up to about 500 mg of the preparation per day for a 70 kg subject, with dosages of from about 1.0 mg to about 200 mg of the preparation per day being more commonly used. It will be understood that determining an appropriate dosage may be achieved using routine experimentation, by constructing a matrix of values and testing different points in the matrix.

Local delivery of the preparations of the present invention, such as, for example, topical application, may be carried out, e.g., by means of a spray, perfusion, double balloon catheters, stent, incorporated into vascular grafts or stents, hydrogels used to coat balloon catheters, or other well established methods. In any event, the pharmaceutical compositions should provide a quantity of the preparation sufficient to effectively treat the subject.

The pharmaceutical compositions of the invention may further comprise other bioactive agents, such as, e.g., non-Factor VII-related coagulants or anticoagulants.

Sustained Release Preparations

Examples of sustained-release preparations include semipermeable matrices of solid hydrophobic polymers containing the polypeptide or conjugate, the matrices having a suitable form such as a film or microcapsules. Examples of sustained-release matrices include polyesters, hydrogels (for example, poly(2-hydroxyethyl-methacrylate) or poly(vinylalcohol)), polylactides, copolymers of L-glutamic acid and ethyl-L-glutamate, non-degradable ethylenevinyl acetate, degradable lactic acid-glycolic acid copolymers such as the ProLease® technology or Lupron Depot@ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for long periods such as up to or over 100 days, certain hydrogels release proteins for shorter time periods. When encapsulated polypeptides remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

The following non-limiting examples illustrate certain aspects of the invention.

EXAMPLES

Example 1

Glycopegylation of Product with High Sialic Content

Polyethylene glycol-CMP-sialic acid (PEG-CMPSA) is prepared by covalently attaching PEG with mw 10.000 Da to sialic acid.

Factor VIIa with 87-99% content of sialic acid is treated with sialidase, e.g., as described in U.S. Pat. No. 5,272,066, and re-sialylated with sialyltransferase using PEG-CMPSA as donor molecule (e.g., as described in U.S. Pat. No. 6,399,336). After the PEGylation reaction has reached maximal incorporation, CMPSA is added to the reaction mixture to cap any exposed terminal galactose.

Incorporation of PEGylated sialic acid is analyzed by SDS-PAGE, CE-PAGE, isoelectric focusing gels, and CE-IEF.

94-100% sialic acid is incorporated; a mean of 1-4 PEG groups are incorporated.

Example 2

Glycopegylation of Product with Medium Sialic Content

Polyethylene glycol-CMP sialic acid (PEG-CMPSA) is prepared by covalently attaching PEG with mw 10.000 Da to sialic acid.

Factor VIIa with 87-93% content of sialic acid is treated with sialyltransferase using PEG-CMPSA as donor molecule (e.g., as described in U.S. Pat. No. 6,399,336). After the PEGylation reaction has reached maximal incorporation, CMPSA is added to the reaction mixture to cap any exposed terminal galactose.

Incorporation of PEGylated sialic acid is analyzed by SDS-PAGE, CE-PAGE, isoelectric focusing gels, and CE-IEF.

87-100% sialic acid is incorporated; a mean of 0.1-0.5 PEG groups are incorporated.

Example 3

Pegylated cytidine 5'-monophospho-sialic acid derivative (CMP-SA-PEG): N-Acetyl-$O^2$-methyl-9-amino-9-deoxy-neuraminic acid methyl ester (10 mg, 0.031 mmol, prepared according to Isecke, R.; Brossmer, R., *Tetrahedron* 1994, 50(25), 7445-7460) is dissolved in water (2 ml), and mPEG-SBA (170 mg, 0.03 mmol, 5 kDa, Shearwater 2M450H01)) is added. The mixture is stirred at ambient temperature until completion according to TLC. The solvent is removed by lyophilization, and the residue redissolved in a 1:1 mixture of methanol and 0.1 M NaOH solution (5 ml). The mixture is stirred at room temperature for 1 h, then passed through a column of Dowex 50W-X8 ($H^+$) resin at 4° C. and lyophilized. The residue is then redissolved in water (5 ml), Dowex 50W-X8 ($H^+$) resin is added and the mixture is stirred until completed by TLC.

Cytidine 5'-monophospho analogues of sialic acid derivatives of general formula I is in general prepared according to E. S. Simon, M. D. Bednarski and G. M. Whitesides, *J. Am. Chem. Soc.*, 1998, 110, 7159-7163 as described in the following way: Cytidine 5'-monophosphoneuraminic acid synthetase is dissolved in a solution of 9-pegylated N-Acetyl-9-amino-9-deoxy-neuraminic acid (prepared as described above), and added to a solution of CTP. The mixture is adjusted to pH 8.5 and $MgCl_2.6H_2O$ is added. The reaction is stirred at room temperature, and 1N NaOH is added via a peristaltic pump to keep the pH near 8.5. When $^1H$-NMR on an aliquot shows completion, the product is isolated by standard ion-exchange chromatography.

Example 4

FVIIa (1 mg) dissolved in 1 ml of 0.1 M sodium acetate pH 5.5 is oxidized a level of its glycans at room temperature for 30 min. with 10 mM sodium periodate. The solution is then dialyzed against 100 mM sodium acetate pH 5.5. After dialysis, PEG-C(O)—$NHNH_2$ (prepared by hydrazinolysis of mPEG-SBA (2 mg, 5 kDa, Shearwater 2M450H01)) is mixed with the oxidized FVIIa, and allowed to react overnight at room temperature with gentle shaking. The FVIIa-PEG conjugate solution thus obtained is dialyzed (dialysis membranes with 10 kDa cut-off) against 100 mM Tris-HCl buffer, pH 7.5 and stored at 4° C.

Pharmacological Methods

The following assays are useful for determining biological activity, half-life and bioavailability of Factor VII and Factor VII-related polypeptides.

Assay (I)

In Vitro Hydrolysis Assay

The following method can be used to assay Factor VIIa bioactivity. The assay is carried out in a microtiter plate (MaxiSorp, Nunc, Denmark). The chromogenic substrate D-Ile-Pro-Arg-p-nitroanilide (S-2288, Chromogenix, Sweden), at a final concentration of 1 mM, is added to Factor VIIa (final concentration 100 nM) in 50 mM Hepes, pH 7.4, containing 0.1 M NaCl, 5 mM $CaCl_2$ and 1 mg/ml bovine serum albumin. The absorbance at 405 nm is measured continuously in a SpectraMax™ 340 plate reader (Molecular Devices, USA). The absorbance developed during a 20-minute incubation, after subtraction of the absorbance in a blank well containing no enzyme, is used to calculate the ratio between the activities of a test and a reference Factor VIIa.

Assay (II)

In Vitro Proteolysis Assay

The following method can be used to assay Factor VIIa bioactivity. The assay is carried out in a microtiter plate (MaxiSorp, Nunc, Denmark). Factor VIIa (10 nM) and Factor X (0.8 microM) in 100 µl 50 mM Hepes, pH 7.4, containing 0.1 M NaCl, 5 mM $CaCl_2$ and 1 mg/ml bovine serum albumin, are incubated for 15 min. Factor X cleavage is then stopped by the addition of 50 µl 50 mM Hepes, pH 7.4, containing 0.1 M NaCl, 20 mM EDTA and 1 mg/ml bovine serum albumin. The amount of Factor Xa generated is measured by addition of the chromogenic substrate Z-D-Arg-Gly-Arg-p-nitroanilide (S-2765, Chromogenix, Sweden), final concentration 0.5 mM. The absorbance at 405 nm is measured continuously in a SpectraMax™ 340 plate reader (Molecular Devices, USA). The absorbance developed during 10 minutes, after subtraction of the absorbance in a blank well containing no FVIIa, is used to calculate the ratio between the proteolytic activities of a test and a reference Factor VIIa.

Assay (III)

Measurement of Functional In Vivo Half-Life

Measurement of in vivo biological half-life can be carried out in a number of ways as described in the literature. An example of an assay for the measurement of in vivo half-life of rFVIIa and variants thereof is described in FDA reference number 96-0597. Briefly, FVIIa clotting activity is measured in plasma drawn prior to and during a 24-hour period after administration of the conjugate, polypeptide or composition. The median apparent volume of distribution at steady state is measured and the median clearance determined.

Assay (IV)

Bioavailability of Factor VII Polypeptides

Bioavailability may, for example, be measured in a dog model as follows: The experiment is performed as a four leg cross-over study in 12 Beagle dogs divided in four groups. All animals receive a test preparation A and a reference preparation B at a dose of about 90 µg/kg in a glycylglycine buffer (pH 5.5) containing sodium chloride (2.92 mg/ml), calcium chloride dihydrate (1.47 mg/ml), mannitol (30 mg/ml) and polysorbate 80. Blood samples are withdrawn at 10, 30, and 60 minutes and 2, 3, 4, 6 and 8 hours following the initial administration. Plasma is obtained from the samples and Factor VII is quantified by ELISA.

Bioavailability of each sample is expressed as the dose-adjusted area under the plasma concentration curve for Factor VII (AUC/dose). The relative bioavailability is expressed as the ratio between the mean AUC/dose of the test and reference preparation×100 and 90% confidence limits for the relative bioavailability is calculated.

The invention claimed is:

1. A preparation comprising a Factor VII polypeptide comprising SEQ ID NO: 1, wherein the Factor VII polypeptide has (1) a valine substituted with aspartic acid at position 158 of SEQ ID NO: 1, (2) a glutamic acid substituted with valine at position 296 of SEQ ID NO: 1 and (3) a methionine substituted with glutamine at position 298 of SEQ ID NO: 1, and wherein the Factor VII polypeptide comprises one or more oligosaccharide chains, wherein the oligosaccharide chains are selected from the group consisting of asparagine-linked oligosaccharide chains, serine-linked oligosaccharide chains, and combinations thereof, and wherein at least one of said oligosaccharide chains is covalently attached to at least one polyethylene glycol (PEG).

2. A preparation comprising a Factor VII polypeptide comprising SEQ ID NO: 1 or Factor VII related polypeptide, wherein the Factor VII polypeptide has a serine substituted with alanine at position 52 as of SEQ ID NO: 1, wherein the Factor VII polypeptide comprises one or more oligosaccharide chains, wherein the oligosaccharide chains are selected from the group consisting of asparagine-linked oligosaccharide chains, serine-linked oligosaccharide chains, and combinations thereof, and wherein at least one of said oligosaccharide groups is covalently attached to at least one polyethylene glycol (PEG).

* * * * *

SEQUENCE LISTING

```
<160> NUMBER OF SEQ ID NOS: 1

<210> SEQ ID NO 1
<211> LENGTH: 406
<212> TYPE: PRT
<213> ORGANISM: Human
<220> FEATURE:
<221> NAME/KEY: MISC. FEATURE
<222> LOCATION: (1)..(406)
<223> OTHER INFORMATION: Xaa=Gamma Carboxyglutamic Acid

<400> SEQUENCE: 1

Ala Asn Ala Phe Leu Xaa Xaa Leu Arg Pro Gly Ser Leu Xaa Arg Xaa
1               5                   10                  15

Cys Lys Xaa Xaa Gln Cys Ser Phe Xaa Xaa Ala Arg Xaa Ile Phe Lys
            20                  25                  30

Asp Ala Xaa Arg Thr Lys Leu Phe Trp Ile Ser Tyr Ser Asp Gly Asp
        35                  40                  45
```

```
Gln Cys Ala Ser Ser Pro Cys Gln Asn Gly Gly Ser Cys Lys Asp Gln
    50                  55                  60

Leu Gln Ser Tyr Ile Cys Phe Cys Leu Pro Ala Phe Glu Gly Arg Asn
65              70                  75                  80

Cys Glu Thr His Lys Asp Asp Gln Leu Ile Cys Val Asn Glu Asn Gly
                85                  90                  95

Gly Cys Glu Gln Tyr Cys Ser Asp His Thr Gly Thr Lys Arg Ser Cys
            100                 105                 110

Arg Cys His Glu Gly Tyr Ser Leu Leu Ala Asp Gly Val Ser Cys Thr
        115                 120                 125

Pro Thr Val Glu Tyr Pro Cys Gly Lys Ile Pro Ile Leu Glu Lys Arg
    130                 135                 140

Asn Ala Ser Lys Pro Gln Gly Arg Ile Val Gly Gly Lys Val Cys Pro
145                 150                 155                 160

Lys Gly Glu Cys Pro Trp Gln Val Leu Leu Leu Val Asn Gly Ala Gln
                165                 170                 175

Leu Cys Gly Gly Thr Leu Ile Asn Thr Ile Trp Val Val Ser Ala Ala
            180                 185                 190

His Cys Phe Asp Lys Ile Lys Asn Trp Arg Asn Leu Ile Ala Val Leu
        195                 200                 205

Gly Glu His Asp Leu Ser Glu His Asp Gly Asp Glu Gln Ser Arg Arg
    210                 215                 220

Val Ala Gln Val Ile Ile Pro Ser Thr Tyr Val Pro Gly Thr Thr Asn
225                 230                 235                 240

His Asp Ile Ala Leu Leu Arg Leu His Gln Pro Val Val Leu Thr Asp
                245                 250                 255

His Val Val Pro Leu Cys Leu Pro Glu Arg Thr Phe Ser Glu Arg Thr
            260                 265                 270

Leu Ala Phe Val Arg Phe Ser Leu Val Ser Gly Trp Gly Gln Leu Leu
        275                 280                 285

Asp Arg Gly Ala Thr Ala Leu Glu Leu Met Val Leu Asn Val Pro Arg
    290                 295                 300

Leu Met Thr Gln Asp Cys Leu Gln Gln Ser Arg Lys Val Gly Asp Ser
305                 310                 315                 320

Pro Asn Ile Thr Glu Tyr Met Phe Cys Ala Gly Tyr Ser Asp Gly Ser
                325                 330                 335

Lys Asp Ser Cys Lys Gly Asp Ser Gly Gly Pro His Ala Thr His Tyr
            340                 345                 350

Arg Gly Thr Trp Tyr Leu Thr Gly Ile Val Ser Trp Gly Gln Gly Cys
        355                 360                 365

Ala Thr Val Gly His Phe Gly Val Tyr Thr Arg Val Ser Gln Tyr Ile
    370                 375                 380

Glu Trp Leu Gln Lys Leu Met Arg Ser Glu Pro Arg Pro Gly Val Leu
385                 390                 395                 400

Leu Arg Ala Pro Phe Pro
                405
```